(12) United States Patent
Kubota et al.

(10) Patent No.: US 8,970,846 B2
(45) Date of Patent: Mar. 3, 2015

(54) OPTICAL IMAGE MEASUREMENT APPARATUS

(75) Inventors: Atsushi Kubota, Tokyo (JP); Tomoyoshi Abe, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 298 days.

(21) Appl. No.: 13/517,936

(22) PCT Filed: Nov. 16, 2010

(86) PCT No.: PCT/JP2010/006719
§ 371 (c)(1),
(2), (4) Date: Jun. 20, 2012

(87) PCT Pub. No.: WO2011/077634
PCT Pub. Date: Jun. 30, 2011

(65) Prior Publication Data
US 2012/0257211 A1    Oct. 11, 2012

(30) Foreign Application Priority Data
Dec. 25, 2009    (JP) ................................. 2009-293979

(51) Int. Cl.
G01B 9/02    (2006.01)
A61B 3/10    (2006.01)
G01N 21/47   (2006.01)

(52) U.S. Cl.
CPC ............ *A61B 3/102* (2013.01); *G01N 21/4795* (2013.01); *G01B 9/02091* (2013.01)
USPC .......................................... 356/479; 356/497

(58) Field of Classification Search
USPC ................................................ 356/479, 497
See application file for complete search history.

(56) References Cited

U.S. PATENT DOCUMENTS 4,706,657 A   11/1987   Miyagi
6,377,349 B1   4/2002   Fercher
(Continued)

FOREIGN PATENT DOCUMENTS

| JP | 04-035855 Y2 | 8/1992 |
| JP | 09-276232 A | 10/1997 |
| JP | 11-325849 A | 11/1999 |
| JP | 2002-139421 A | 5/2002 |
| JP | 2006-153838 A | 6/2006 |

(Continued)

OTHER PUBLICATIONS

Igarashi, K.; "Optical Axis Adjustment Method"; In: Toshiba Technical Disclosure Bulletin, vol. 10-48; May 25, 1992; pp. 105-108. (cited in ISR).
International Search Report for PCT/JP2010/006719; Dec. 21, 2010.

*Primary Examiner* — Jonathan Hansen
*Assistant Examiner* — Jonathon Cook
(74) *Attorney, Agent, or Firm* — Pearne & Gordon LLP

(57) ABSTRACT

A main controller 211 controls a fiber-end drive mechanism 140 and an attenuator 121 with reference to the received-light amount of interference light LC to cause the following operations (1) and (2) to be executed alternately: (1) moving an emission end 116 to increase the received-light amount to at least an upper limit; and (2) changing the light amount of reference light LR to decrease the received-light amount to at least a lower limit. When the received-light amount specified by an received-light-amount specifying part 212 decreases in response to the movement of the emission end 116 in (1), the main controller 211 controls the fiber-end drive mechanism 140 to return the relative position to the immediately preceding status of this change. The main controller 211 leads the received-light amount of interference light LC by a CCD image sensor 120 to a target value by controlling the attenuator 121 to change the light amount of interference light LC.

12 Claims, 9 Drawing Sheets

(56) References Cited

U.S. PATENT DOCUMENTS

| | | |
|---|---|---|
| 7,345,770 B2 | 3/2008 | Chan et al. |
| 7,557,928 B2 | 7/2009 | Ueno |
| 7,859,680 B2 | 12/2010 | Abe et al. |
| 2007/0127033 A1* | 6/2007 | Ueno .......................... 356/497 |
| 2009/0219515 A1* | 9/2009 | Spennemann et al. .......... 356/73 |

FOREIGN PATENT DOCUMENTS

| | | |
|---|---|---|
| JP | 2007-024677 A | 2/2007 |
| JP | 2007-151622 A | 6/2007 |
| JP | 2008-203246 A | 9/2008 |
| JP | 2008-259544 A | 10/2008 |
| JP | 2009-087240 A | 4/2009 |

* cited by examiner

OPTICAL IMAGE MEASUREMENT APPARATUS

TECHNICAL FIELD

The present invention relates to an optical image measurement apparatus configured to form images of a measured object by using optical coherence tomography (OCT).

BACKGROUND ART

In recent years, OCT that forms images of the surface morphology and internal morphology of an object by using a light beam from a laser light source or the like has attracted attention. Unlike an X-ray CT apparatus, optical coherence tomography is noninvasive to human bodies, and is therefore expected to be utilized in the medical field and biological field. For example, in the ophthalmology, devices that form images of a fundus and cornea or the like are in a practical stage.

Patent Document 1 discloses a device to which OCT is applied. This device has such a configuration that: a measuring arm scans an object by a rotary deflection mirror (a Galvano mirror); a reference arm is provided with a reference mirror; and an interferometer is mounted at the outlet to analyze, by a spectrometer, the intensity of an interference light of light fluxes from the measurement arm and the reference arm. Moreover, the reference arm is configured to gradually change the light flux phase of the reference light by discontinuous values.

The device of Patent Document 1 uses a technique of so-called "Fourier Domain OCT." That is to say, the device irradiates a low-coherence light beam to an object, superposes the reflected light and the reference light to generate an interference light, and acquires the spectral intensity distribution of the interference light to execute Fourier transform, thereby imaging the morphology in the depth direction (the z-direction) of the object. The technique of this type is also called Spectral Domain.

Furthermore, the device described in Patent Document 1 is provided with a Galvano mirror that scans with a light beam (a signal light), and is thereby configured to form an image of a desired measurement target region of the object. Because this device is configured to scan with the light beam only in one direction (the x-direction) orthogonal to the z-direction, an image formed by this device is a two-dimensional tomographic image in the depth direction (the z-direction) along the scanning direction (the x-direction) of the light beam.

Patent Document 2 discloses a technique of scanning with a signal light in the horizontal direction (x-direction) and the vertical direction (y-direction) to form a plurality of two-dimensional tomographic images in the horizontal direction, and acquiring and imaging three-dimensional tomographic information of a measured range based on the tomographic images. As the three-dimensional imaging, for example, a method of arranging and displaying a plurality of tomographic images in the vertical direction (referred to as stack data or the like), and a method of executing a rendering process on a plurality of tomographic images to form a three-dimensional image are considered.

Patent Documents 3 and 4 disclose other types of OCT devices. Patent Document 3 describes an OCT device that images the morphology of an object by sweeping the wavelength of light that is irradiated to an object, acquiring the spectral intensity distribution based on an interference light obtained by superposing the reflected lights of the light of the respective wavelengths on the reference light, and executing Fourier transform. Such an OCT device is called a Swept Source type or the like. The Swept Source type is a kind of the Fourier Domain type.

Further, Patent Document 4 describes an OCT device that irradiates a light having a predetermined beam diameter to an object and analyzes the components of an interference light obtained by superposing the reflected light and the reference light, thereby forming an image of the object in a cross-section orthogonal to the travelling direction of the light. Such an OCT device is called a full-field type, en-face type or the like.

Patent Document 5 discloses an example of applying OCT to the ophthalmologic field. The device described in Patent Document 5 comprises a mechanism that adjusts the relative position (i.e., relative location and/or direction) between an emission end of a light guiding part that guides interference light and a light-receiving surface in order to properly project the interference light onto the light-receiving surface of the light-receiving part.

In addition, in the ophthalmologic field, before OCT was applied, a fundus camera, a slit lamp, etc. were used as devices for observing an eye (e.g., see Patent Documents 6 and 7). The fundus camera is a device that photographs the fundus oculi by projecting illumination light onto the eye and receiving the reflected light from the fundus oculi. The slit lamp is a device that obtains an image of the cross-section of the cornea by cutting off the light section of the cornea using slit light.

The device with OCT is superior relative to the fundus camera, etc. in that high-definition images can be obtained, further in that tomographic images and three-dimensional images can be obtained, etc.

PRIOR ART DOCUMENTS

Patent Documents

[Patent Document 1]
Japanese Unexamined Patent Application Publication No. Hei 11-325849
[Patent Document 2]
Japanese Unexamined Patent Application Publication No. 2002-139421
[Patent Document 3]
Japanese Unexamined Patent Application Publication No. 2007-24677
[Patent Document 4]
Japanese Unexamined Patent Application Publication No. 2006-153838
[Patent Document 5]
Japanese Unexamined Patent Application Publication No. 2008-203246
[Patent Document 6]
Japanese Unexamined Patent Application Publication No. Hei 9-276232
[Patent Document 7]
Japanese Unexamined Patent Application Publication No. 2008-259544

DISCLOSURE OF THE INVENTION

Problem that the Invention is to Solve

Although OCT is a highly effective technique as described above, it is problematic in that it is difficult to properly maintain the received-light amount of interference light by the light-receiving part. This received-light amount corresponds to the intensity of the electric light output by the light-receiving part as a result of receiving interference light, also referred to as interference sensitivity. When the received-light amount is too great, a saturation status results and, conversely, when it is too little, information included in the interference light cannot be effectively detected.

Factors affecting the received-light amount include not only the relative positional relationship between the emission end of the light guiding part and the light-receiving surface of the light-receiving part described in Patent Document 5, but also the variation in various types of light involved in OCT, particularly the variation in the light amount of reference light, etc. This variation in the light amount results from displacement of optical members such as a reference mirror. Many of such displacements occur due to changes in the environment (particularly temperature changes) where the device is placed, so it is difficult to correct displacement of each optical member in each case.

In addition, although it is not impossible to adjust the received-light amount using the mechanism indicated in Patent Document 5 and a light-amount-adjustment mechanism such as an attenuator, cumbersome and time-consuming work must be performed in which the adjustment of the former is carried out followed by the adjustment of the latter and the adjustment of the latter is carried out followed by the adjustment of the former.

This invention resolves the above-mentioned problem, with the purpose of providing an optical image measurement apparatus capable of easily and quickly adjusting the received-light amount of interference light by the light-receiving part.

Means for Solving the Problem

In order to achieve the aforementioned objects, an invention according to Claim 1 is an optical image measurement apparatus comprising: an interferometer that splits low-coherence light into signal light and reference light and generates interference light by superposing the signal light that has passed through a measured object and the reference light that has passed through a reference optical path; a light guiding part that guides the generated interference light; a spectral part that divides the interference light emitted from an emission end of the light guiding part into spectra; a light-receiving part that receives the interference light divided into spectra and outputs a signal; a specifying part that specifies a received-light amount of the interference light by the light-receiving part based on the output signal; a first changing part that changes the relative position between the emission end and a light-receiving surface of the light-receiving part; a second changing part for changing the light amount of the interference light projected onto the light-receiving part; a controller that controls the first changing part and the second changing part based on the specified received-light amount and leads the received-light amount of the interference light by the light-receiving part to a target value; and an image forming part that forms an image of the measured object based on the results of the interference light received by the light-receiving part after the received-light amount has been led to the target value.

Further, an invention according to Claim 2 is the optical image measurement apparatus according to Claim 1, wherein the controller controls the first changing part based on the received-light amount specified by the specifying part and changes the relative position to increase the received-light amount.

Further, an invention according to Claim 3 is the optical image measurement apparatus according to Claim 1, wherein: the light-receiving part is a line sensor that has multiple light-receiving elements arranged one-dimensionally; and the first changing part changes the relative position by moving the emission end and/or the light-receiving part in a direction intersecting the direction of the arrangement of the multiple light-receiving elements.

Further, an invention according to Claim 4 is the optical image measurement apparatus according to Claim 1, wherein the second changing part comprises: a shielding member that shields part of the cross-section of the low-coherence light, the signal light, the reference light and/or the interference light; and a drive part that moves the shielding member; and wherein, the controller controls the drive part based on the received-light amount specified by the specifying part and moves the shielding member to change a shield region in the cross-section.

Further, an invention according to Claim 5 is the optical image measurement apparatus according to Claim 1, wherein the controller causes the following operations to be performed alternately: a first operation that controls the first changing part and the second changing part with reference to the received-light amount that is sequentially specified by the specifying part and changes the relative position to increase the received-light amount to at least an upper limit in a predefined range; and a second operation that changes the light amount to decrease the received-light amount to at least a lower limit in the predefined range, when the specified received-light amount decreases in response to a change in the relative position in the first operation, the controller causes the first changing part to perform a third operation that changes the relative position to the immediately preceding status of this change; and further the controller causes the second changing part to perform a fourth operation that changes the light amount and leads the received-light amount to the target value.

Further, an invention according to Claim 6 is the optical image measurement apparatus according to Claim 5, wherein the controller in the first operation causes the following operations to be performed alternately until the received-light amount above the upper limit is specified by the specifying part: an operation that causes the first changing part to change the relative position in a predefined direction by a predefined distance; and an operation that causes the specifying part to specify the received-light amount.

Further, an invention according to Claim 7 is the optical image measurement apparatus according to Claim 5, wherein the controller in the second operation causes the following operations to be performed alternately until the received-light amount below the lower limit is specified by the specifying part: an operation that causes the second changing part to decrease the light amount by a predefined amount; and an operation that causes the specifying part to specify the received-light amount.

Further, an invention according to Claim 8 is the optical image measurement apparatus according to Claim 5, wherein the controller in the third operation causes the first changing part to change the relative position to the immediately preceding status in a direction opposite to the predefined direction.

Further, an invention according to Claim 9 is the optical image measurement apparatus according to Claim 1, wherein the controller: with reference to the received-light amount that is sequentially specified by the specifying part, by controlling the first changing part and changing the relative position in a predefined direction, detects the peak of the specified received-light amount; controls the first changing part in response to the peak being detected, and changes the relative position to the position where the peak has been detected in a direction opposite to the predefined direction; and further controls the second changing part and changes the light amount to lead the received-light amount to the target value.

Further, an invention according to Claim 10 is the optical image measurement apparatus according to Claim 1, wherein the controller: with reference to the received-light amount that is sequentially specified by the specifying part, by controlling the first changing part and changing the relative position in a predefined direction, increases the received-light amount until reaching a limit value for the light-receiving part; controls the first changing part and further changes the relative position in the predefined direction until the specified received-light amount becomes less than the limit value; controls the first changing part and changes the relative position between the emission end and the light-receiving surface of the light-receiving part to a third relative position between a first relative position where the received-light amount reaches the limit value and a second relative position where it becomes less than the limit value; controls the second changing part and changes the light amount to lead the received-light amount to the target value.

Further, an invention according to Claim 11 is the optical image measurement apparatus according to Claim 10, wherein the third relative position is an intermediate position between the first relative position and the second relative position.

Further, an invention according to Claim 12 is the optical image measurement apparatus according to Claim 10, wherein the controller, in the operation leading the received-light amount to the target value, controls the second changing part with reference to the received-light amount that is sequentially specified by the specifying part.

Further, an invention according to Claim 13 is the optical image measurement apparatus according to Claim 10, wherein the controller: based on an interval between the first relative position and the second relative position, calculates the amount of change in the light amount for changing the specified received-light amount from the limit value to the target value; and in the operation leading the received-light amount to the target value, controls the second changing part to change the light amount by the calculated amount of change.

Effect of the Invention

The optical image measurement apparatus related to the present invention, based on the received-light amount of interference light by the light-receiving part, automatically performs a change of the relative position between the emission end of the light guiding part and the light-receiving surface of the light-receiving part, and a change of the light amount of signal light or reference light, respectively, and operates to lead the received-light amount of interference light by the light-receiving part to a target value. Therefore, it is possible to easily and quickly adjust the received-light amount of interference light by the light-receiving part.

MODE FOR CARRYING OUT THE INVENTION

An example of an embodiment of an optical image measurement apparatus according to the present invention will be described in detail with reference to the drawings.

The optical image measurement apparatus according to the present invention forms tomographic images of a measured object using optical coherence tomography. This optical image measurement apparatus uses optical coherence tomography of the type in which spectral components of the interference light are detected. It should be noted that an image obtained by optical coherence tomography is sometimes referred to as an OCT image. Furthermore, a measuring action for forming an OCT image is sometimes referred to as an OCT measurement.

In the following embodiments, a configuration to which a Fourier-Domain-type is applied will be described in detail. To be specific, in these embodiments, similar to a device disclosed in Patent Document 5, an optical image measurement apparatus that is capable of obtaining both tomographic images and photographed image of a fundus will be picked up. It should be noted that the measured object according to the present invention is not limited to an eye (a fundus).

Configuration

Figure 1:
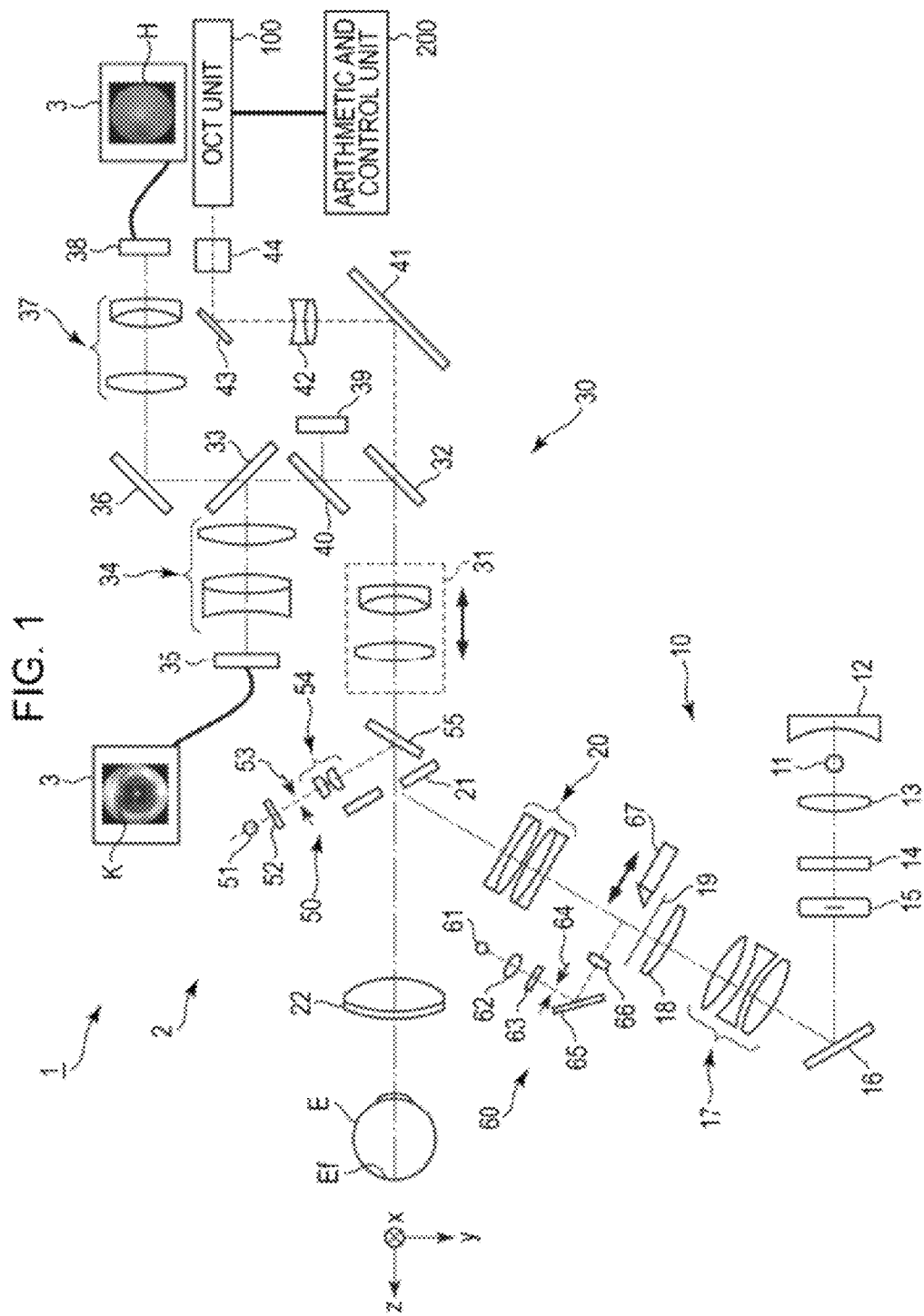
FIG. 1 is a schematic view showing an example of a configuration of an embodiment of an optical image measurement apparatus (fundus observation apparatus) according to the present invention.
Figure 2:
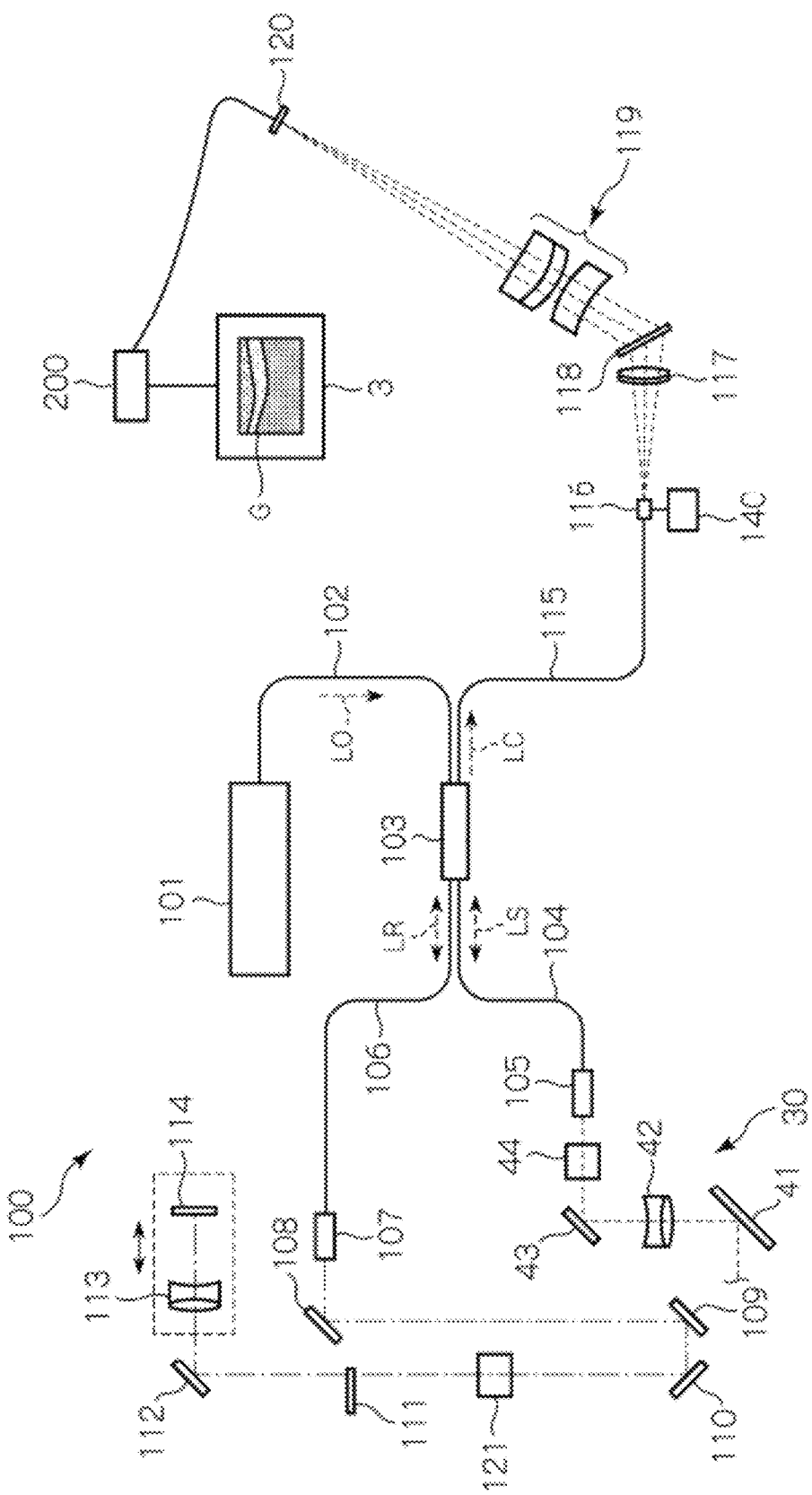
FIG. 2 is a schematic view showing an example of a configuration of an embodiment of an optical image measurement apparatus (fundus observation apparatus) according to the present invention.

A fundus observation apparatus (optical image measurement apparatus) 1, as shown in FIG. 1 and FIG. 2, includes a retinal camera unit 2, an OCT unit 100, and an arithmetic and control unit 200. The retinal camera unit 2 has almost the same optical system as a conventional retinal camera. The OCT unit 100 is provided with an optical system for obtaining an OCT image of a fundus. The arithmetic and control unit 200 is provided with a computer that executes various arithmetic processes, control processes, and so on.

Retinal Camera Unit

The retinal camera unit shown in FIG. 1 is provided with an optical system for forming a 2-dimensional image (fundus image) representing the surface morphology of the fundus Ef of an eye E. Fundus images include observation images, photographed images, etc. The observation image is, for example, a monochrome moving image formed at a prescribed frame rate using near-infrared light. The observation image may be an image of an anterior eye part of the eye E. The photographed image is, for example, a color image captured by flashing visible light. It should be noted that the retinal camera unit 2 may also be configured so as to be capable of capturing other types of images such as a fluorescein angiography image, an indocyanine green fluorescent image, and an autofluorescent image.

The retinal camera unit 2 is provided with a chin rest and a forehead placement for retaining the face of the subject, similar to a conventional retinal camera. Moreover, like a conventional retinal camera, the retinal camera unit 2 is provided with an illumination optical system 10 and an imaging optical system 30. The illumination optical system 10 irradiates an illumination light to the fundus Ef. The imaging optical system 30 guides a fundus reflected light of the illumination light to imaging devices (CCD image sensors 35, 38). Moreover, the imaging optical system 30 guides a signal light LS coming from the OCT unit 100 to the fundus Ef, and guides the signal light propagated through the fundus Ef to the OCT unit 100.

An observation light source 11 of the illumination optical system 10 comprises, for example, a halogen lamp. Light (observation illumination light) output from the observation light source 11 is reflected by a reflection mirror 12 with a curved reflection surface, and becomes near infrared after passing through a visible cut filter 14 via a condenser lens 13. Furthermore, the observation illumination light is once converged near an imaging light source 15, reflected by a mirror 16, and passes through relay lenses 17, 18, diaphragm 19, and relay lens 20. Then, the observation illumination light is reflected on the peripheral part (the surrounding region of an aperture part) of an aperture mirror 21 and illuminates the fundus Ef via an object lens 22.

The fundus reflection light of the observation illumination light is refracted by the object lens 22, passes through the aperture part formed in the center region of the aperture mirror 21, passes through a dichroic mirror 55 and, travels through a focusing lens 31, and is reflected by a dichroic mirror 32. Furthermore, the fundus reflection light passes through a half-mirror 40 and forms an image on the light receiving surface of the CCD image sensor 35 by a condenser lens 34 after being reflected by a dichroic mirror 33. The CCD image sensor 35 detects, for example, the fundus reflection light at a prescribed frame rate. An image (observation image) K based on the fundus reflection light detected by the CCD image sensor 35 is displayed on a display device 3.

The imaging light source 15 consists of, for example, a xenon lamp. The light (imaging illumination light) output from the imaging light source 15 is irradiated to the fundus Ef via a route that is similar to the observation illumination light. The fundus reflection light of the imaging illumination light is guided to the dichroic mirror 33 via the same route as that of the observation illumination light, passes through the dichroic mirror 33, and forms an image on the light receiving surface of the CCD image sensor 38 by a condenser lens 37 after being reflected by a mirror 36. An image (photographed image) H based on the fundus reflection light detected by the CCD image sensor 38 is displayed on the display device 3. It should be noted that the display device 3 for displaying an observation image K and the display device 3 for displaying a photographed image H may be the same or different.

An LCD (Liquid Crystal Display) 39 displays a fixation target or a visual target for measuring eyesight. The fixation target is a visual target for fixing the eye E, and is used when photographing a fundus or performing an OCT measurement.

Part of the light output from the LCD 39 is reflected by a half-mirror 40, reflected by the dichroic mirror 32, passes through the aperture part of the aperture mirror 21 via the focusing lens 31 as well as a dichroic mirror 55, is refracted by the object lens 22 and projected to the fundus Ef.

By changing a display position of the fixation target on the screen of the LCD 39, it is possible to change a fixation position of the eye E. As the fixation position of the eye E, there are a position for acquiring an image centered on the macula of the fundus Ef, a position for acquiring an image centered on the optic papilla, a position for acquiring an image centered on the fundus center between the macula and the optic papilla, and so on, for example, as in conventional retinal cameras.

Furthermore, as with conventional fundus cameras, the retinal camera unit 2 is provided with an alignment optical system 50 and a focus optical system 60. The alignment optical system 50 generates a target (alignment target) for matching the position (alignment) of the device optical system with respect to the eye E. The focus optical system 60 generates a target (split target) for matching the focus with respect to the eye Ef.

Light (alignment light) output from the LED (Light Emitting Diode) 51 of the alignment optical system 50 is reflected by the dichroic mirror 55 via diaphragms 52, 53 and a relay lens 54, passes through the aperture part of the aperture mirror 21, and is projected onto the cornea of the eye E by the object lens 22.

Part of cornea reflection light of the alignment light is transmitted through the dichroic mirror 55 via the object lens 22 and the aperture part, passes through the focusing lens 31, is reflected by the dichroic mirror 32, transmitted through the half-mirror 40, reflected by the dichroic mirror 33, and projected onto the light receiving surface of the CCD image sensor 35 by the condenser lens 34. An image (alignment target) captured by the CCD image sensor 35 is displayed on the display device 3 along with the observation image K. A user conducts alignment by an operation that is the same as conventional fundus cameras. It should be noted that alignment may be performed, by an arithmetic and control unit 200, as a result of analyzing the position of the alignment target and moving the optical system.

In order to conduct focus adjustment, the reflection surface of a reflection rod 67 is provided in a slanted position on the light path of the illumination optical system 10. Light (focus light) output from an LED 61 of the focus optical system 60 passes through a relay lens 62, is split into two light fluxes by a split target plate 63, passes through a two-hole diaphragm 64, is reflected by a mirror 65, and is reflected after an image is formed once on the reflection surface of the reflection rod 67 by a condenser lens 66. Furthermore, the focus light is reflected at the aperture mirror 21 via the relay lens 20 and an image is formed on the fundus Ef by the object lens 22.

The fundus reflection light of the focus light passes through the same route as the cornea reflection light of the alignment light and is detected by the CCD image sensor 35. A light (split target) captured by the CCD image sensor 35 is displayed on the display device 3 along with an observation image K. The arithmetic and control unit 200, as in the past, analyzes the position of the split target, and moves the focusing lens 31 and the focus optical system 60 for focusing. It should be noted that focusing may be performed manually while visually recognizing the split target.

An optical path including a mirror 41, collimator lens 42, and Galvano mirrors 43, 44 is provided behind the dichroic mirror 32. The optical path is connected to the OCT unit 100.

The Galvano mirror 44 performs scanning with a signal light LS from the OCT unit 100 in the x-direction. The Galvano mirror 43 performs scanning with a signal light LS in the y-direction. Scanning may be performed with the signal light LS in an arbitrary direction in the xy-plane due to the two Galvano mirrors 43 and 44.

OCT Unit

The OCT unit 100 is provided with an optical system for obtaining a tomographic image of the fundus Ef (see FIG. 2). The optical system has a similar configuration to a conventional Fourier-Domain-type OCT device. That is to say, the optical system is provided with an interferometer configured to split low-coherence light into signal light and reference light and generates interference light by superposing the signal light that has passed through the fundus Ef and the reference light that has passed through a reference optical path. Furthermore, the optical system is configured to detect the spectral components of the interference light generated by the interferometer. This detection result (detection signal) is transmitted to the arithmetic and control unit 200.

A light source unit 101 outputs a broadband low-coherence light L0. The low-coherence light L0, for example, includes near-infrared wavelength bands (about 800-900 nm) and has a coherence length of about tens of micrometer. Moreover, it is possible to use, as the low-coherence light L0, near-infrared light having wavelength bands that are impossible to be detected by human eyes, for example, infrared light having the center wavelength of about 1050-1060 nm.

The light source unit 101 is configured to include light output device, such as an SLD (super luminescent diode), SOA (Semiconductor Optical Amplifier) and the like.

The low-coherence light L0 output from the light source unit 101 is guided to a fiber coupler 103 by an optical fiber 102 and split into signal light LS and reference light LR. It should be noted that the fiber coupler 103 acts both as a means to split light (splitter) as well as a means to synthesize light (coupler), but herein the same is conventionally referred to as a "fiber coupler."

The signal light LS is guided by the optical fiber 104 and becomes a parallel light flux by a collimator lens unit 105. Furthermore, the signal light LS is reflected by Galvano mirrors 44 and 43, converged by the collimator lens 42, reflected by the mirror 41, transmitted through a dichroic mirror 32, and irradiated to the fundus Ef after passing through a route that is the same as the light from the LCD 39. The signal light LS is scattered and reflected at the fundus Ef. The scattered light and the reflection light are sometimes all together referred to as the fundus reflection light of the signal light LS. The fundus reflection light of the signal light LS progresses along the same route in the reverse direction and is guided to the fiber coupler 103.

The reference light LR is guided by an optical fiber 106 and becomes a parallel light flux by a collimator lens unit 107. Furthermore, the reference light LR is reflected by mirrors 108, 109, 110, passed through an attenuator 121, dimmed by an ND (Neutral Density) filter 111, and reflected by a mirror 112, with the image formed on a reflection surface of a reference mirror 114 by a collimator lens 113. The reference light LR reflected by the reference mirror 114 progresses along the same route in the reverse direction and is guided to the fiber coupler 103. It should be noted that an optical element for dispersion compensation (pair prism, etc.) and/or an optical element for polarization correction (wave plate, etc.) may also be provided for the optical path (reference optical path) of the reference light LR.

Now, an attenuator 121 will be described. As described previously, reference light LR passing through the attenuator 121 is a parallel pencil. The attenuator 121 is a device that changes the light amount of the reference light LR.

As a specific example thereof, the attenuator 121 is configured to change the amount of light by shielding part of the cross-section of the reference light LR. The attenuator 121 is equipped with a shielding member that can be inserted and removed relative to the optical path of the reference light LR, as well as a drive part that moves this shielding member. The drive part includes, for example, a stepping motor. The drive part is controlled by an arithmetic and control unit 200 to gradually change the position of the shielding member. Thereby, the shielding member gradually shields the cross-section of the reference light LR. That is, the attenuator 121 can gradually change the light amount of the reference light LR. Thereby, a shield region made by the shielding member in the cross-section of the reference light LR is changed.

The configuration of the attenuator 121 is not limited to that described above. It is possible to apply an attenuator of any known configuration to the present invention. The attenuator 121 is for changing the light amount of interference light LC projected onto a CCD image sensor 120 by changing the light amount of the reference light LR, which is an example of a "second changing part" in the present invention.

The fiber coupler 103 superposes the fundus reflection light of the signal light LS and the reference light LR reflected by the reference mirror 114. Interference light LC thus generated is guided by an optical fiber 115 and output from an exit end 116. Furthermore, the interference light LC is converted to a parallel light flux by a collimator lens 117, spectrally divided (spectrally decomposed) by a diffraction grating 118, converged by the convergence lens 119, and projected onto the light receiving surface of a CCD image sensor 120. The diffraction grating 118 shown in FIG. 2 is of the transmission type, but the reflection type can also be used.

The CCD image sensor 120 is for example a line sensor (image sensor in which multiple CCD elements are arranged one-dimensionally), and detects the respective spectral components of the spectrally decomposed interference light LC and converts the components into electric charges. The CCD image sensor 120 accumulates these electric charges and generates a detection signal. Furthermore, the CCD image sensor 120 transmits the detection signal to the arithmetic and control unit 200.

It should be noted that CCD image sensor 120 may be an area sensor (image sensor in which multiple CCD elements are arranged two-dimensionally). In this case, predefined CCD elements that are arranged one-dimensionally among the multiple CCD elements are used to detect spectral components.

The optical fiber 115 is an example of a "light guiding part" of the present invention. The diffraction grating 118 is an example of a "spectral part" of the present invention. The CCD image sensor 120 is an example of a "light-receiving part" of the present invention.

The emission end 116 of the optical fiber 115 is configured to be movable. This is described as follows. With OCT measurement, it is necessary to accurately project the spectral components of the interference light relative to CCD elements comprising the CCD image sensor 120. Therefore, it is necessary to conform the direction of the arrangement of the CCD elements and the spreading direction of the spectral components of the interference light LC as much as possible and adjust the relative positional relationship between the emission end 116 and the light-receiving surface of the CCD image sensor 120 so that each CCD element accurately receives the spectral components to be received.

In this embodiment, this relative position is changed by changing the position of the emission end 116. As an example of the configuration at that end, a fiber-end drive mechanism is described in Patent Document 5. In this embodiment, this fiber-end drive mechanism is to be used (indicated by the symbol 140).

The fiber-end drive mechanism 140 is configured to include an actuator such as a stepping motor, and a transfer mechanism that transfers the drive force output by this actuator, for example. This transfer mechanism is connected to, for example, a site of the optical fiber 115 other than its end face (i.e., the interference light LC emission end face) and transfers the drive force developed by the actuator to the emission end 116.

The fiber-end drive mechanism 140 moves the emission end 116 in the direction parallel to the end face of the optical fiber 115 or in the direction perpendicular to the end face. Therefore, the emission end 116 is moved three-dimensionally with the direction of the end face fixed. Furthermore, the fiber-end drive mechanism 140 moves the position of the emission end 116 to change the direction of the end face.

In this embodiment, at least one (referred to as the "relative position") of the relative positional relationships between the emission end 116 and the light-receiving surface of the CCD image sensor 120 and the relative direction between the end face of the emission end 116 and the light-receiving surface is changed. That is, the fiber-end drive mechanism 140 may change the relative positional relationship alone, the relative direction alone, or possibly both.

In this embodiment, although the configuration to change the position of the emission end 116 is employed, in place of this, it is also possible to employ the configuration to change the position of the CCD image sensor 120. Moreover, it is also possible to change both the position of the emission end 116 and the position of the CCD image sensor 120.

The fiber-end drive mechanism 140 is an example of the "first changing part" in the present invention. In particular, the fiber-end drive mechanism 140 changes the relative position between the emission end 116 and the light-receiving surface by moving the emission end 116 in the direction intersecting the direction of the arrangement of the CCD elements. The "intersecting direction" is, for example, the direction perpendicular to the direction of the arrangement. Moreover, in order to deal with the case in which the spread direction of the spectral components of the interference light LC is inclined relative to the direction of the arrangement, the fiber-end drive mechanism 140 may have a function to rotate the emission end 116 around the axial direction of the optical fiber 115.

Although a Michelson-type interferometer is employed in this embodiment, it is possible to employ any type of interferometer such as a Mach-Zehnder-type as necessary. Instead of a CCD image sensor, other types of image sensors, such as a CMOS (Complementary Metal Oxide Semiconductor) image sensor, can be used.

In this embodiment, the second changing part is established in the reference optical path. One of the reasons thereof is that the device is used in the ophthalmologic field. That is, considering there is a limitation on the light amount of illumination light (herein the signal light LS) in order to avoid damage to the eye, in addition to the fact that the signal light LS reflected from the fundus oculi is weak, it is necessary to maintain the proper light amount of the reference light LR. When the light amount of the reference light LR is too much, compared to that of the signal light LS, subtle information included in the signal light LS is masked by the reference light LR and suitable interference light LC cannot be obtained. Conversely, when the light amount of the reference light LR is insufficient, the signal light LS and the reference light LR do not interfere well. In this embodiment, for this reason, the attenuator 121 is disposed in the reference optical path to adjust the light amount of the reference light LR.

If the device related to the present invention is used in other fields, it is also possible to establish a second changing part in the signal optical path. Moreover, it is also possible to establish a second changing part in the optical path for low-coherence light L0 or interference light LC. If a second changing part is established in the low-coherence light L0, for example, the second changing part can be disposed to change the light amount of low-coherence light L0 (which is desirably a parallel pencil) emitting from the light source unit 101 and propagating through the space, and configured to cause the low-coherence light L0 that has passed through this to enter the optical fiber 102. If the second changing part is established in the optical path for interference light LC, for example, the second changing part can be disposed between the fiber coupler 103 and a spectrometer (i.e., diffraction grating 118) (which is desirably a position where the interference light LC is a parallel pencil). Moreover, the second changing part may be respectively established in at least two optical paths for the low-coherence light L0, signal light LS, reference light LR, and interference light LC. In this case, the second changing parts may be controlled independently or all operations may be linked.

Arithmetic and Control Unit

A configuration of the arithmetic and control unit 200 will be described. The arithmetic and control unit 200 analyzes the detection signals inputted from the CCD image sensor 120, and forms an OCT image of the fundus Ef. An arithmetic process for this is the same as that of a conventional Fourier-Domain-type OCT device.

Further, the arithmetic and control unit 200 controls each part of the retinal camera unit 2, the display device 3 and the OCT unit 100. For example, the arithmetic and control unit 200 causes an OCT image such as a tomographic image G (see FIG. 2) of the fundus Ef to be displayed on the display device 3.

As control of the retinal camera unit 2, the arithmetic and control unit 200 executes: control of action of the observation light source 101, the imaging light source 103 and LED's 51 and 61; control of action of the LCD 39; control of movement of the focusing lens 31; control of movement of the reflection rod 67; control of movement of the focus optical system 60; control of action of the respective Galvano mirrors 43 and 44; and so on.

Further, as control of the OCT unit 100, the arithmetic and control unit 200 executes: control of action of the light source unit 101; control of movement of the reference mirror 114 and the collimator lens 113; control of action of the CCD image sensor 120; control of action of the attenuator 121; control of action of the fiber-end drive mechanism 140; and so on.

The arithmetic and control unit 200 includes a microprocessor, a RAM, a ROM, a hard disk drive, a communication interface, and so on, as in conventional computers. The storage device such as the hard disk drive stores a computer program for controlling the fundus observation apparatus 1. The arithmetic and control unit 200 may be provided with a circuit board dedicated for forming OCT images based on detection signals from the CCD image sensor 120. Moreover, the arithmetic and control unit 200 may be provided with operation devices (input devices) such as a keyboard and a mouse, and/or display devices such as LCD.

The retinal camera unit 2, display device 3, OCT unit 100, and arithmetic and control unit 200 may be integrally configured (that is, within a single case), or configured as separate bodies.

Control System

Figure 3:
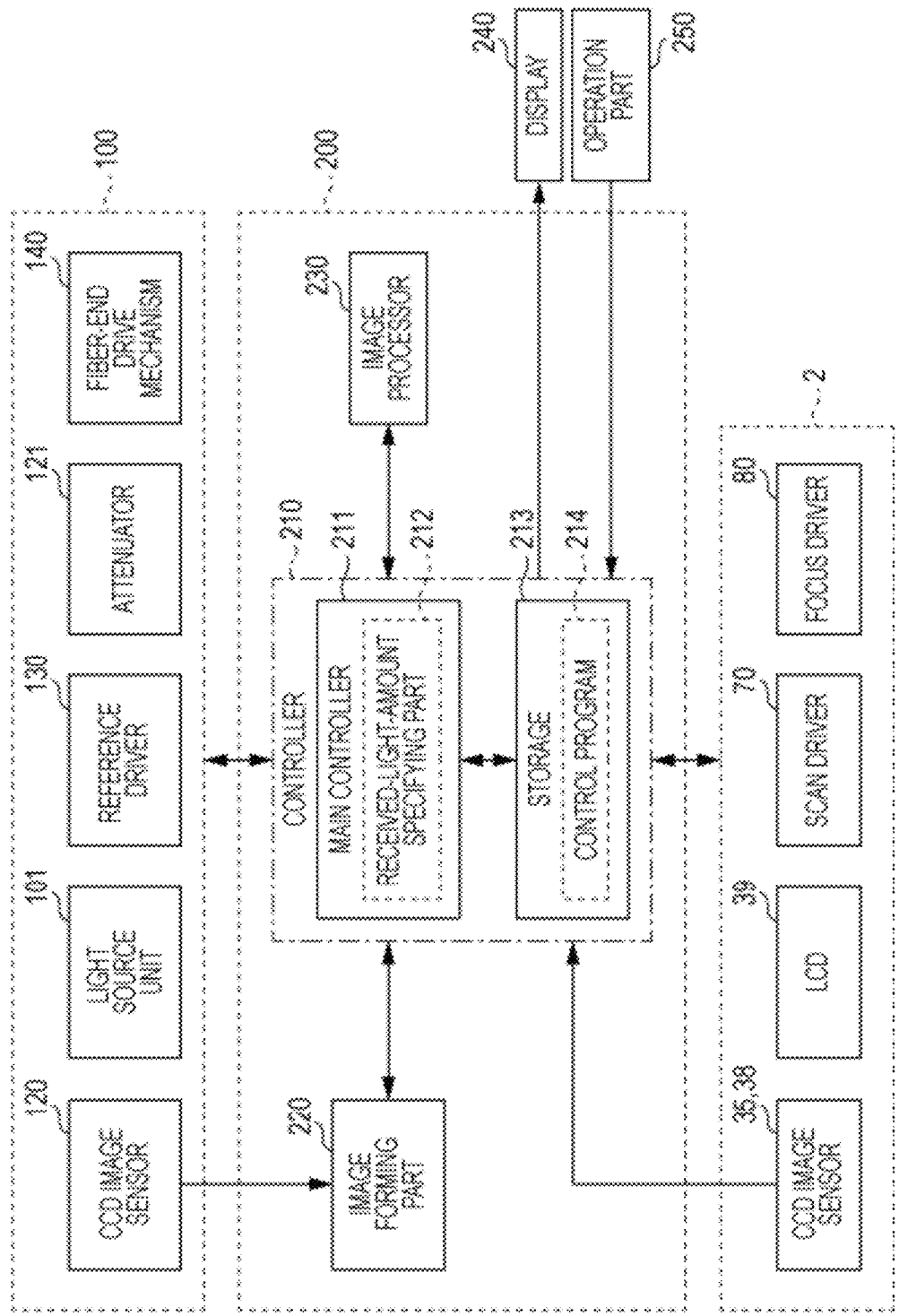
FIG. 3 is a schematic block diagram showing an example of a configuration of an embodiment of an optical image measurement apparatus (fundus observation apparatus) according to the present invention.

A configuration of a control system of the fundus observation apparatus 1 will be described with reference to FIG. 3.

Controller

The control system of the fundus observation apparatus 1 has a configuration centered on a controller 210 of the arithmetic and control unit 200. The controller 210 includes, for example, the aforementioned microprocessor, RAM, ROM, hard disk drive, and communication interface.

The controller 210 is provided with a main controller 211 and storage 213. The main controller 211 performs the aforementioned various kinds of control. Specifically, the main controller 211 controls a scan driver 70 as well as a focus driver 80 of the retinal camera unit 2, and further controls a reference driver 130, the attenuator 121 and the fiber-end drive mechanism 140 of the OCT unit 100. The main controller 211 is an example of a "controller" of the invention.

The scan driver 70 is configured, for example, including a servo motor and independently changes the facing direction of the Galvano mirrors 43 and 44.

The focus driver 80 is configured, for example, including a pulse motor and moves the focusing lens 31 in the optical axis direction. Thereby, the focus position of light towards the fundus Ef is changed.

The reference driver 130 is configured, for example, including a pulse motor and integrally moves the collimator lens 113 as well as the reference mirror 114 along the travelling direction of the reference light LR.

The main controller 211 controls the fiber-end drive mechanism 140 based on the received-light amount that is specified by a received-light-amount specifying part 212 described later. Thereby, the main controller 211 moves the emission end 116 to increase the received-light amount (i.e., the relative position between the emission end 116 and the light-receiving surface is changed). This processing corresponds to more properly projecting the spectral components of the interference light LC onto the light-receiving surface, i.e., correcting the position of projecting the spectral components onto the light-receiving surface.

The main controller 211 controls the attenuator 121 based on the received-light amount that is specified by the received-light-amount specifying part 212. Thereby, the main controller 211 moves the shielding member of the attenuator 121 and changes the shield region in the cross-section of the reference light LR. This processing corresponds to changing the light amount of the reference light LR contributing to the generation of the interference light LC.

The main controller 211 executes a process of writing data into the storage 213, and a process of reading out the data from the storage 213.

The main controller 211 is equipped with the received-light-amount specifying part 212. The received-light-amount specifying part 212 specifies the amount of the interference light LC received by the CCD image sensor 120 based on the signal (aforementioned detection signal) output from the CCD image sensor 120. The received-light-amount specifying part 212 is an example of the "specifying part" in the present invention.

The received-light amount is affected by the light amount of the interference light LC and the projection status of the interference light LC relative to the light-receiving surface of the CCD image sensor 120. In this embodiment, the adjustment operations for these two factors are linked to obtain a suitable received-light amount.

The light amount of the interference light LC is determined by the light amount of the signal light LS and the light amount of the reference light LR. In this embodiment, the light amount of the signal light LS is not adjusted, so the light amount of the interference light LC reflects the light amount of the reference light LR. The light amount of the reference light LR is adjusted by the attenuator 121 as described previously.

The projection status of the interference light LC relative to the light-receiving surface includes the projection position of the interference light LC relative to the light-receiving surface of the CCD image sensor 120, as well as the projection direction of the interference light LC relative to the light-receiving surface. In addition, only one of these may be taken into account.

If the projection position of the interference light LC relative to the light-receiving surface is displaced, some or all of the CCD elements arranged on the light-receiving surface may not receive the interference light LC. Thus, some or all of the spectral components of the interference light LC may not be detected and proper OCT images cannot be formed.

Moreover, if the projection direction of the interference light LC relative to the light-receiving surface is displaced, each spectral component of the interference light LC enters from an improper direction relative to the CCD elements arranged on the light-receiving surface. Thus, the received-light amount of a spectral component received that is detected by each CCD element no longer reflects the actual light amount (intensity) and no proper OCT images can be formed.

Although the details are described later, in this embodiment, by executing the adjustment of the light amount of the reference light LR (i.e., the light amount of the interference light LC), as well as the adjustment of the projection status of the interference light LC relative to the light-receiving surface, while monitoring the received-light amount of the interference light LC, it is attempted to ease and accelerate the adjustment operation for the received-light amount of the interference light LC by the CCD image sensor 120.

The storage 213 stores various kinds of data. The data stored in the storage 213 is, for example, image data of OCT images, image data of fundus images, and eye information. The eye information includes information on the eye, for example, information on a subject such as a patient ID and a name, information on identification of left eye or right eye, and so on.

Furthermore, a control program 214 is stored in the storage 213 in advance. The main controller 211 causes characteristic actions (described latter) of the present embodiment to be performed by controlling each part of the apparatus based on the control program 214.

Image Forming Part

An image forming part 220 forms image data of a tomographic image of the fundus Ef based on the detection signals from the CCD image sensor 120. Like the conventional Fourier-Domain OCT, this process includes processes such as noise elimination (noise reduction), filtering, and FFT (Fast Fourier Transform).

The image forming part 220 includes, for example, the aforementioned circuit board and communication interface. It should be noted that "image data" and the "image" presented based on the image data may be identified with each other in this specification.

The image forming part 220 is an example of an "image forming part" of the present invention. The image forming part may include an image processor 230 (in particular, its part forming three-dimensional images and tomographic images) as described later.

Image Processor

An image processor 230 executes various image processing and analysis on images formed by the image forming part 220. For example, the image processor 230 executes various correction processes such as luminance correction and dispersion correction of images.

Further, the image processor 230 executes, for example, an interpolation process of interpolating pixels between tomographic images formed by the image forming part 220, thereby forming image data of a three-dimensional image of the fundus Ef.

Image data of a three-dimensional image refers to image data that the positions of pixels are defined by the three-dimensional coordinates. The image data of a three-dimensional image is, for example, image data composed of three-dimensionally arranged voxels. This image data is referred to as volume data, voxel data, or the like. For displaying an image based on the volume data, the image processor 230 executes a rendering process (such as volume rendering and MIP (Maximum Intensity Projection)) on this volume data, and forms image data of a pseudo three-dimensional image taken from a specific view direction. On a display device such as the display 240, this pseudo three-dimensional image is displayed.

Further, it is also possible to form stack data of a plurality of tomographic images as the image data of a three-dimensional image. Stack data is image data obtained by three-dimensionally arranging a plurality of tomographic images obtained along a plurality of scanning lines, based on the positional relation of the scanning lines. That is to say, stack data is image data obtained by expressing a plurality of tomographic images defined by originally individual two-dimensional coordinate systems by a three-dimensional coordinate system (namely, embedding into a three-dimensional space).

The image processor 230 can form a tomographic image in any cross-section based on the image data of a three-dimensional image. This processing is executed, for example, by specifying, for the cross-section manually or automatically designated, a picture element (such as a voxel) located on this cross-section and arranging the specified image elements two-dimensionally to form image data that represents the morphology of the fundus Ef in the cross-section. Such processing enables images to be obtained not only in the cross-section of the original tomographic image (the position of the scanning line for the signal light LS) but also in any desired cross-section.

The image processor 230 includes, for example, the aforementioned microprocessor, RAM, ROM, hard disk drive, circuit board, and so on.

Display and Operation Part

The display 240 is configured including various types of display devices such as the display device 3. The operation part 250 is configured including an operation device equipped with the arithmetic and control unit 200, and various kinds of operation devices provided with the case of the fundus observation apparatus 1 or its outside.

The display 240 and the operation part 250 do not need to be composed as separate devices. For example, like a touch panel LCD, a device in which the display function and the operation function are integrated can be used.

Scan with Signal Light and OCT Image

A scan with the signal light LS and an OCT image will be described.

The scan aspect of the signal light LS by the fundus observation apparatus 1 is, for example, a horizontal scan, vertical scan, cruciform scan, radial scan, circular scan, concentric scan, and helical scan. These scan aspects are selectively used as necessary in consideration of an observation site of the fundus, an analysis target (the retinal thickness or the like), a time required to scan, the accuracy of a scan, and so on.

A horizontal scan is a scan with the signal light LS in the horizontal direction (x-direction). The horizontal scan includes an aspect of scanning with the signal light LS along a plurality of scanning lines extending in the horizontal direction arranged in the vertical direction (y-direction). In this aspect, it is possible to set any interval between scanning lines. By setting the interval between adjacent scanning lines to be sufficiently narrow, it is possible to form the aforementioned three-dimensional image (three-dimensional scan). A vertical scan is also performed in a similar manner.

A cruciform scan is a scan with the signal light LS along a cross-shape trajectory formed by two linear trajectories (line trajectories) orthogonal to each other. A radial scan is a scan with the signal light LS along a radial trajectory formed by a plurality of line trajectories arranged at predetermined angles. The cruciform scan is an example of the radial scan.

A circular scan is a scan with the signal light LS along a circular trajectory. A concentric scan is a scan with the signal light LS along a plurality of circular trajectories arranged concentrically around a predetermined center position. The circular scan is an example of the concentric scan. A helical scan is a scan with the signal light LS along a helical trajectory while making the turning radius gradually smaller (or greater).

Because the Galvano mirrors 43 and 44 are configured to scan the signal light LS in the directions orthogonal to each other, they are capable of scanning with the signal light LS in the x-direction and the y-direction independently. Moreover, it is possible to scan with the signal light LS along an arbitrary trajectory on the xy-plane by simultaneously controlling the directions of the Galvano mirrors 43 and 44. Thus, it is possible to realize various types of scan aspects as described above.

By scanning the signal light LS in the mode described above, it is possible to form tomographic images of the depth-wise direction (z-direction) along scanning lines (scan trajectory). Moreover, in a case that the interval between scanning lines is narrow, it is possible to form the aforementioned three-dimensional image.

A region on the fundus Ef subjected to scanning by the signal light LS as above, that is a region on the fundus Ef subjected to OCT measurement, is referred to as a scanning region. A scanning region in three-dimensional scanning is a rectangular-shaped region in which multiple horizontal scans are arranged. Furthermore, a scanning region in a concentric circular scan is a disc-shaped region surrounded by the trajectories of a circular scan of a maximum diameter. Moreover, the scanning region in a radial scan is a disc-shaped (or polygonal-shaped) region linking end positions of scanning lines.

Operation

The operation of the fundus observation apparatus 1 is described. The following operation is performed at a predefined timing before measurement. For example, the following operation is performed before shipment, at the time of starting (at the time of power-up), at the time of changing a subject.

First Operational Example

Figure 4:
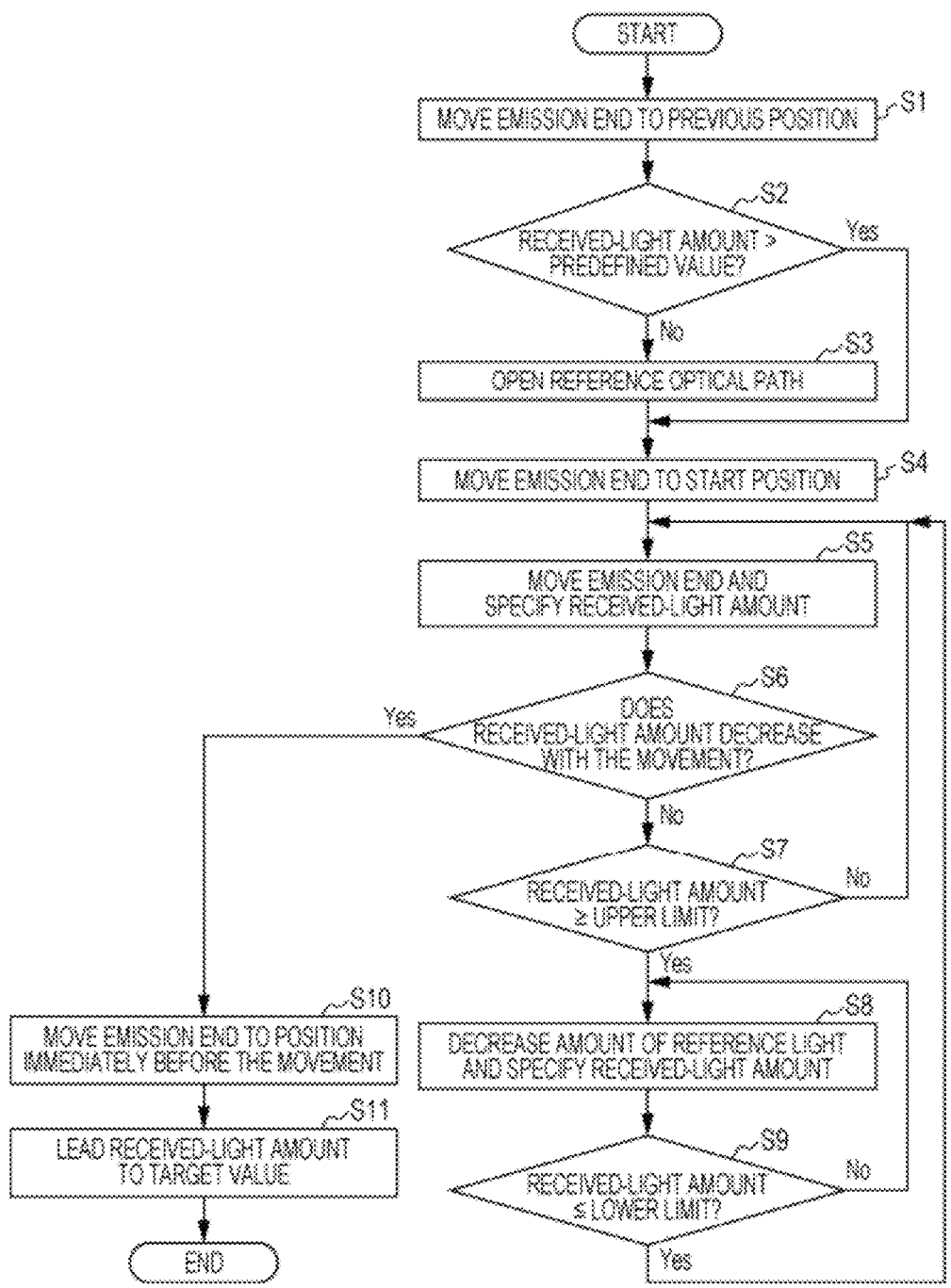
FIG. 4 is a flowchart showing an example of an action of an embodiment of an optical image measurement (fundus observation apparatus) apparatus according to the present invention.

A first operational example is described with reference to FIG. 4 and FIG. 5.

First, the main controller 211 controls the fiber-end drive mechanism 140 to move the emission end 116 to the position in the previous examination (S1). This processing is executed as follows, for example.

As a premise, at every examination, the main controller 211 stores the information indicating the position of the emission end 116 at that time in the storage 213. Every time it adjusts the position of the emission end 116, it may store the information indicating the position after the adjustment. The main controller 211 reads this information from the storage 213 and controls the fiber-end drive mechanism 140 so as to dispose the fiber-end drive mechanism 140 in that position.

Next, the main controller 211 checks if the received-light amount by the CCD image sensor 120 in this status exceeds a predefined value (S2). This predefined value is an arbitrary preset value for determining whether or not the received-light amount is insufficient. This predefined value is set to a lower limit in a predefined range described later, for example. The processing of Step 2 is executed as follows, for example.

The main controller 211 controls the light source unit 101 to cause low-coherence light L0 to be output. The reference light LR based on the low-coherence light L0 reaches the diffraction grating 118 via the reference optical path, fiber coupler 103, optical fiber 115, etc. The diffraction grating 118 divides the reference light LR into spectra. The spectral components thereof are projected onto the light-receiving surface of the CCD image sensor 120. The CCD image sensor 120 that has received the spectral components sends a detection signal to the arithmetic and control unit 200. The received-light-amount specifying part 212 obtains the received-light amount based on this detection signal. The main controller 211 determines whether the obtained received-light amount exceeds a predefined value.

Although the case has been described herein in which there is no measured object ahead of the signal optical path, if there is a measured object ahead of the signal optical path, synthetic light of the signal light LS reflected from the measured object and the reference light LR is received. The received-light-amount specifying part 212 obtains the received-light amount of this synthetic light and the main controller 211 determines whether this received-light amount exceeds a predefined value.

If the received-light amount is equal to or less than the predefined value (S2: No), the main controller 211 controls the attenuator 121 to open the reference optical path, i.e., release the shield against the reference light LR (S3). More specifically, the main controller 211 controls the drive part of the attenuator 121 to retreat the shielding member from the reference optical path.

Subsequently, the main controller 211 controls the fiber-end drive mechanism 140 to move the emission end 116 to a start position (S4). This start position is, for example, a predefined position in the direction perpendicular to the direction of the arrangement of the CCD elements. In the subsequent processing, the emission end 116 is moved in the perpendicular direction. This moving direction is considered to be the direction in which the received-light amount should increase. In addition, if the received-light amount decreases with the movement in this direction, the opposite direction will be the subsequent moving direction. The start position is shown in FIG. 5. The moving direction is the direction indicated by the horizontal axis (emission end position) in FIG. 5. Reference is made to FIG. 5 in the following.

The main controller 211 controls the fiber-end drive mechanism 140 to sequentially move the emission end 116 while causing the received-light-amount specifying part 212 to sequentially execute the processing to specify the received-light amount (S5). With the setting of the moving direction previously described, at least during the initial stage, the received-light amount increases with the movement of the emission end 116 (S6: No). It is when the projection positions of the spectral components passes through the CCD elements that the received-light amount starts to decrease with the movement of the emission end 116.

In this processing, the operation in which the fiber-end drive mechanism 140 moves the emission end 116 in a predefined direction (the aforementioned moving direction) by a predefined distance and the operation in which the received-light-amount specifying part 212 specifies the received-light amount, are performed alternately. The former operation is executed by, for example, sending a predefined pulse number signal to the stepping motor of the fiber-end drive mechanism 140 to drive it. Thereby, the operation is repeatedly performed in which, as the emission end 116 is moved by the predefined distance, the received-light amount is obtained, and as the emission end 116 is further moved by the predefined distance, the received-light amount is obtained. This operation is repeated until the obtained received-light amount is equal to or more than the upper limit (S7: No). This operation is indicated by the symbol A1 in FIG. 5.

In addition, this upper limit is the maximum value in a predefined range that has been preset. This predefined range can be arbitrarily set to the extent that it does not substantially depart from the target value for the received-light amount. This target value is an approximately optimal value for the received-light amount, which is the final value achieved that is led by this operational example. This target value is preset.

When the received-light amount equal to or more than the upper limit is obtained (S7: Yes), the main controller 211 stops the operation of the fiber-end drive mechanism 140 and controls the attenuator 121 to decrease the light amount of reference light LR (S8). Thereby, the light amount of interference light LC decreases and the received-light amount by the CCD image sensor 120 decreases. This is the operation indicated by the symbol B1. Also in this operation, the processing to decrease the light amount of reference light LR by a predefined amount and the processing to specify the received-light amount are repeatedly performed. The former processing is executed by, for example, sending a predefined pulse number signal to the stepping motor of the attenuator 121 to drive it. This operation is repeated until the obtained received-light amount becomes equal to or less than the lower limit (S9: No).

When the received-light-amount equal to or less than the lower limit is obtained (S9: Yes), the main controller 211 stops the operation of the attenuator 121 and controls the fiber-end drive mechanism 140 to restart the movement of the emission end 116 (S5). Thereby, the operation indicated by the symbol A2, the operation indicated by the symbol B2, . . . , the operation indicated by the symbol Ak, and the operation indicated by the symbol Bk are sequentially executed.

The processing in Steps 5 through 9 is repeated until the received-light amount decreases with the movement of the emission end 116 (S6: No). As described previously, the fact that the received-light amount has started to decrease with the movement of the emission end 116 means that the projection positions of the spectral components of the interference light LC has passed through the CCD elements of the CCD image sensor 120.

In addition, because it is possible that the received-light amount decreases temporarily due to the effect of noise, etc., it may be determined whether or not the received-light amount continues to decrease while moving the emission end 116 by a certain distance.

Figure 5:
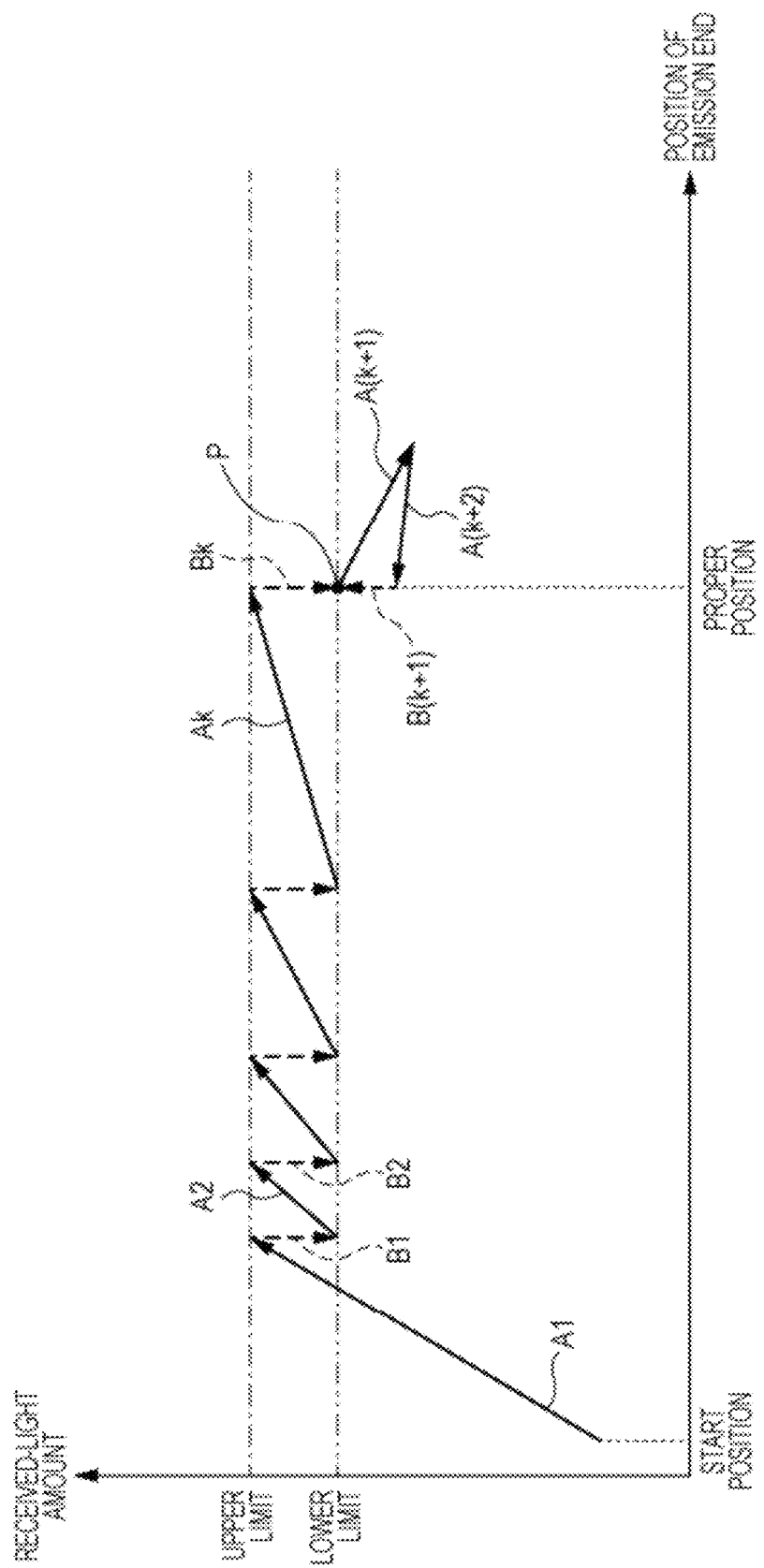
FIG. 5 is a schematic view for explaining an example of an action of an embodiment of an optical image measurement apparatus (fundus observation apparatus) according to the present invention.

When the received-light amount decreases with the movement of the emission end 116 as indicated by the symbol A(k+1) in FIG. 5 (S6: Yes), the main controller 211 controls the fiber-end drive mechanism 140 and reverses the moving direction of the emission end 116 to move the emission end 116 to the position immediately before the movement (i.e., the position where the received-light amount has started to decrease) (S10). This is the operation indicated by the symbol A(k+2). With this operation, the emission end 116 is disposed in a proper position shown in FIG. 5. This proper position is the position of the emission end 116 that realizes a status in which the spectral components of the interference light LC are properly projected onto the CCD elements.

Subsequently, the main controller 211 controls the attenuator 121 and leads the received-light amount to a target value P (S11). This is the operation indicated by the symbol B(k+1). This completes the processing related to this operational example. After such adjustment processing of the received-light amount is completed, the fundus observation apparatus 1 performs OCT measurement and forms an OCT image of the fundus Ef.

According to this operational example, it is possible to perform position adjustment of the emission end 116 so that the spectral components of the interference light LC are properly projected onto the CCD elements while adjusting the light amount of reference light LR (i.e., interference light LC), and tailor the received-light amount to the target value in response to the completion of the position adjustment.

In the operational example above, the predefined range shown in FIG. 5 (the range defined by the upper and lower limits) corresponds to the range of reduction of the received-light amount by the attenuator 121. When the predefined range is set extensively, this range of reduction becomes larger. In this case, in general, the number of times to repeat Steps 5 through 9 is reduced, and the accuracy of the processing to look for the proper position of the emission end 116 is reduced. Conversely, narrowing the predefined range makes this range of reduction smaller. In this case, in general, the number of repetitions increases, and the accuracy of the processing is improved. A user can set the predefined range as appropriate by taking into account these items, needs in the examination, etc.

In the operational example above, the range of reduction of the received-light amount by the attenuator 121 is constant but not limited to this. For example, taking into account the items above concerning the predefined range, it is possible to set the predefined range so that the upper limit and/or lower limit increases or decreases depending on the position of the emission end 116 (horizontal axis in FIG. 5). As an example, it is possible to set the predefined range so as to widen the range of reduction to attempt to reduce the examination time at the beginning of the repetition and also gradually diminish the range of reduction to attempt to improve the processing accuracy.

Second Operational Example

Figure 6:
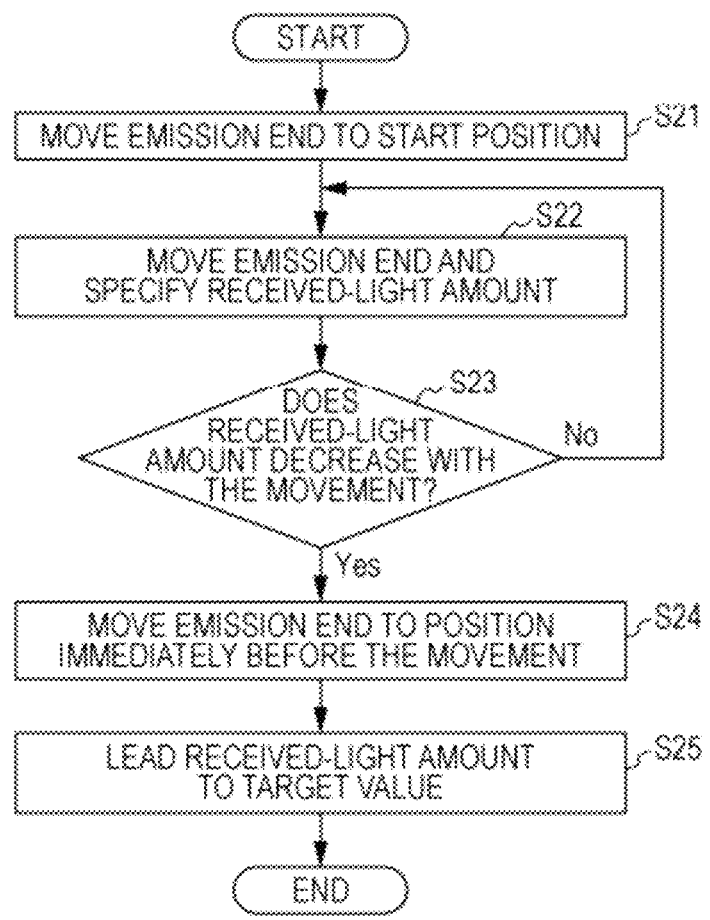
FIG. 6 is a flowchart showing an example of an action of an embodiment of an optical image measurement (fundus observation apparatus) apparatus according to the present invention.
Figure 7:
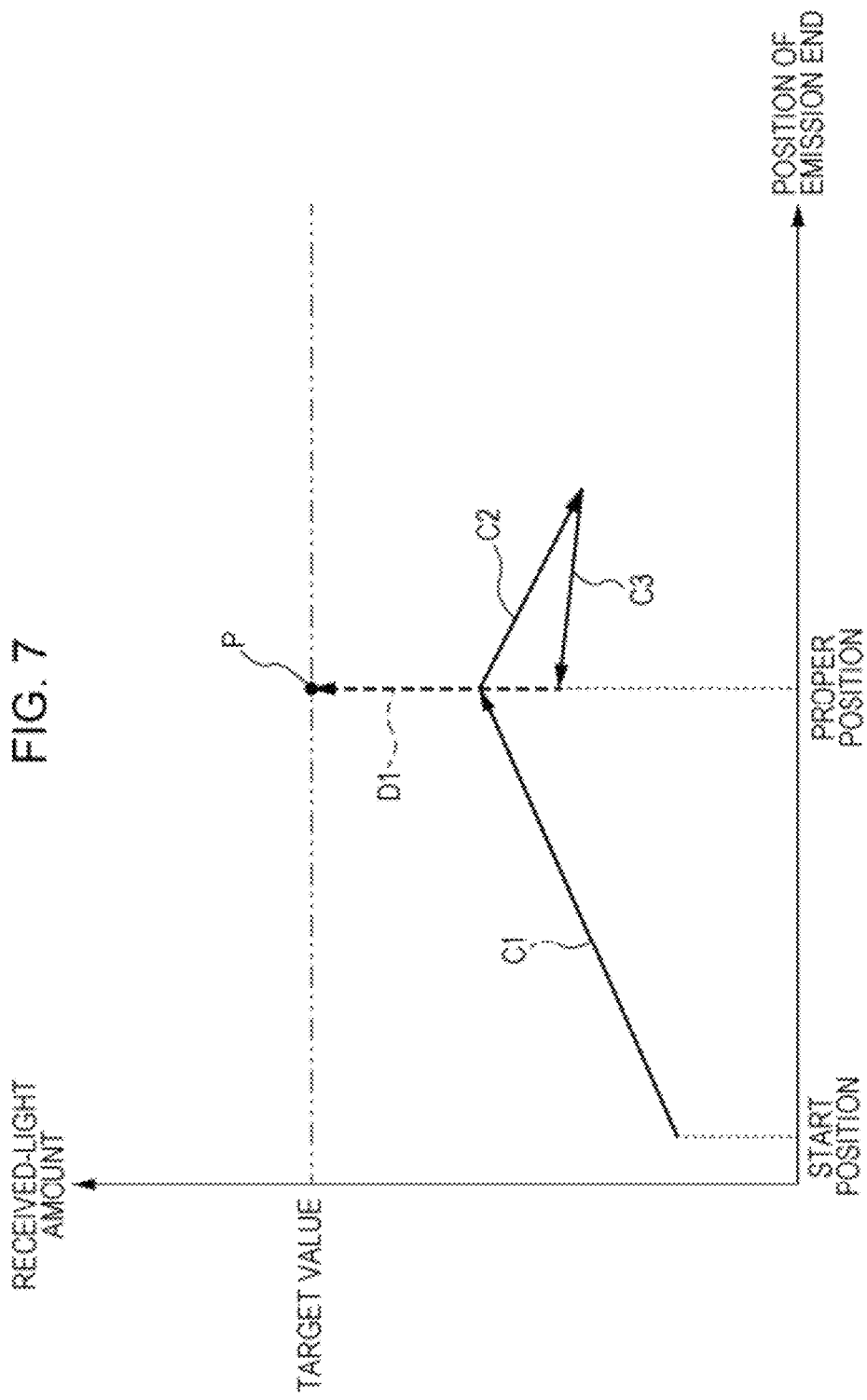
FIG. 7 is a schematic view for explaining an example of an action of an embodiment of an optical image measurement apparatus (fundus observation apparatus) according to the present invention.

A second operational example is described with reference to FIG. 6 and FIG. 7.

First, the main controller 211 controls the fiber-end drive mechanism 140 and moves the emission end 116 to the start position (S21).

Next, the main controller 211, while causing the received-light-amount specifying part 212 to sequentially execute the processing to specify the received-light amount, controls the fiber-end drive mechanism 140 and sequentially moves the emission end 116 (S22). As described previously, at least during the initial stage, the moving direction of the emission end 116 is set to the direction to increase the received-light amount. Step 22 corresponds to the operation indicated by the symbol C1.

Although moving the emission end 116 increases the received-light amount (S23: No), at a certain stage, the received-light amount starts to decrease as indicated by the symbol C2 (S23: Yes). In response to this, the main controller 211 controls the fiber-end drive mechanism 140 and reverses the moving direction of the emission end 116 to move the emission end 116 to the position just prior to the movement (i.e., the position where the received-light amount has started to decrease) (S24). This is the operation indicated by the symbol C3. With this operation, the emission end 116 is disposed in a proper position shown in FIG. 7. This proper position is the position of the emission end 116 that realizes the status in which the spectral components of the interference light LC are properly projected on the CCD elements.

Finally, the main controller 211 controls the attenuator 121 and leads the received-light amount to a target value P (S25). This is the operation indicated by the symbol D1. This completes the processing related to this operational example. The fundus observation apparatus 1 performs OCT measurement and forms an OCT image of the fundus Ef after such adjustment processing of the received-light amount is finished.

According to this operational example, it is possible to automatically adjust the position of the emission end 116 so that the spectral components of the interference light LC are properly projected on the CCD elements and further automatically tailor the received-light amount to the target value. In addition, this operational example is effective if the specified received-light amount is relatively small (e.g., if the shield region by the attenuator 121 is relatively large at the initial stage).

Third Operational Example

Figure 8:
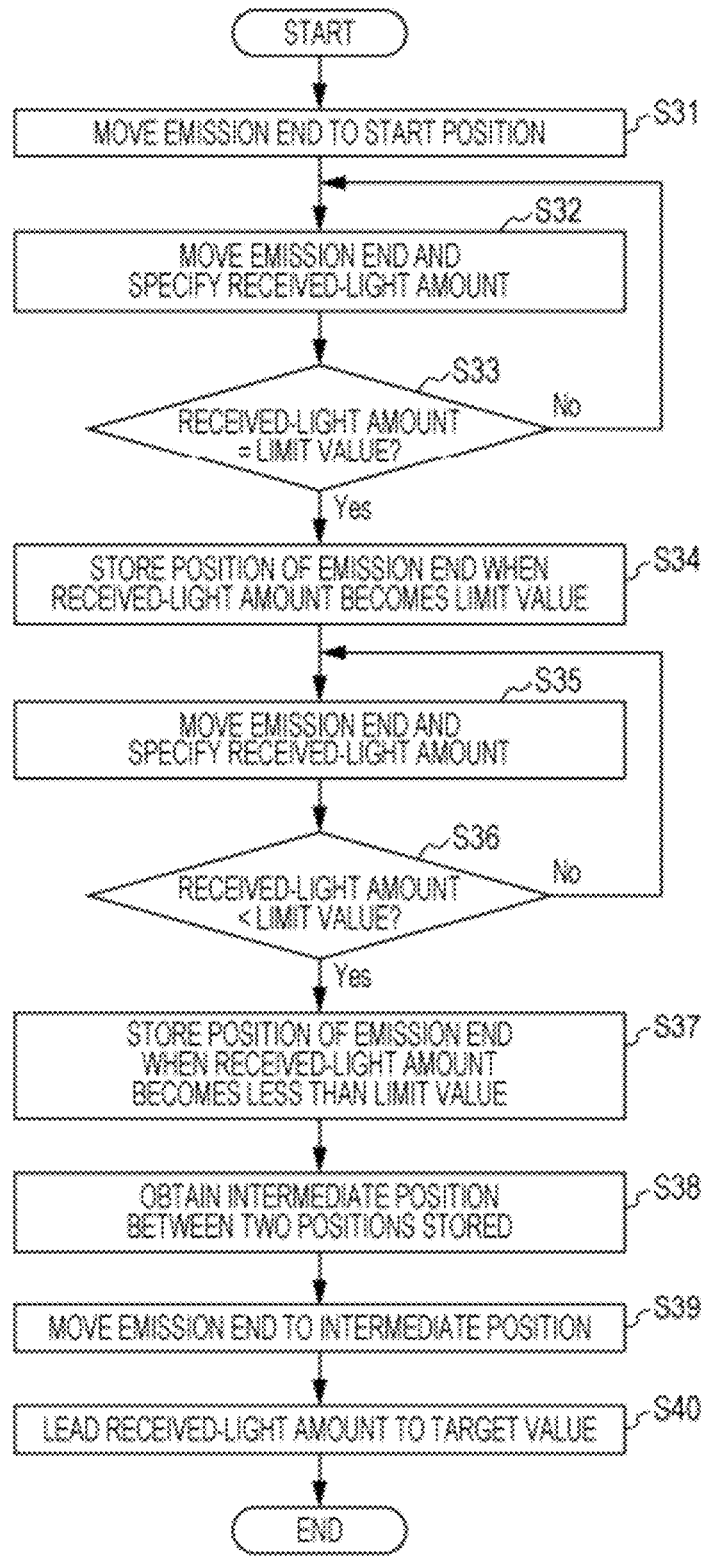
FIG. 8 is a flowchart showing an example of an action of an embodiment of an optical image measurement (fundus observation apparatus) apparatus according to the present invention.
Figure 9:
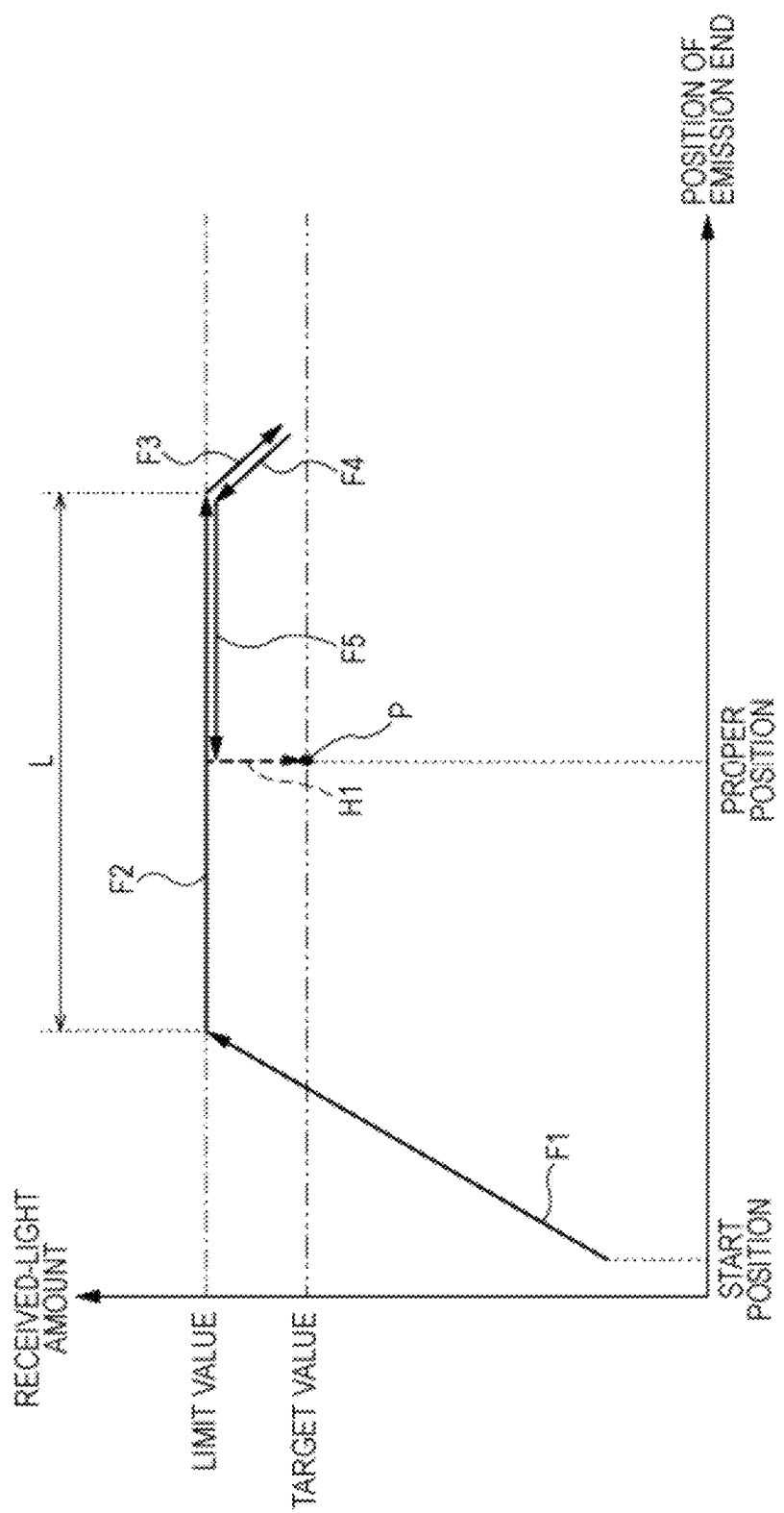
FIG. 9 is a schematic view for explaining an example of an action of an embodiment of an optical image measurement apparatus (fundus observation apparatus) according to the present invention.

A third operational example is described with reference to FIG. 8 and FIG. 9.

First, the main controller 211 controls the fiber-end drive mechanism 140 and moves the emission end 116 to the start position (S31).

Next, the main controller 211 alternately and repeatedly executes the processing to specify the received-light amount and the movement of the emission end 116 (S32, S33: No). This corresponds to the operation indicated by the symbol F1.

With the movement of the emission end 116, the received-light amount gradually increases and reaches the limit value (S33: Yes). This limit value means the saturation status of the received-light amount. The main controller 211 stores the information (first positional information) representing the position of the emission end 116 when the received-light amount has reached the limit value in the storage 213 (S34).

Also, after the received-light amount has reached the limit value, the main controller 211 alternately and repeatedly executes the processing to specify the received-light amount and the movement of the emission end 116 (S35, S36: No). This corresponds to the operation indicated by the symbol F2. At this stage, the specified received-light amount remains the limit value.

When repeatedly performing the processing to specify the received-light amount and the movement of the emission end 116, at a certain stage, the specified received-light amount starts to decrease and becomes less than the limit value (S36: Yes). This corresponds to the operation indicated by the symbol F3. The main controller 211 stores the information (second positional information) representing the position of the emission end 116 when the specified received-light amount has started to decrease in the storage 213 (S37).

Next, the main controller 211 reads the first and second positional information from the storage 213 and obtains the intermediate position between the two positions indicated in these positional information (S38). Then, the main controller 211 controls the fiber-end drive mechanism 140 and moves the emission end 116 to this intermediate position (S39). This corresponds to the operation indicated by the symbols F4 and F5. In addition, the emission end 116 is moved to the intermediate position because it is assumed that the peak of the received-light amount (which cannot be detected because of the saturation status) is located near the intermediate position.

When the emission end 116 has been moved to the intermediate position, the main controller 211 alternately and repeatedly causes the received-light-amount specifying part 212 to execute the processing to specify the received-light amount and causes the attenuator 121 to execute the processing to decrease the light amount of the reference light LR, and leads the specified received-light amount to a target value P (S40). This corresponds to the operation indicated by the symbol H1. This completes the processing related to this operational example. The fundus observation apparatus 1 performs OCT measurement and forms an OCT image of the fundus Ef after such adjustment processing of the received-light amount is finished.

According to this operational example, it is possible to automatically adjust the position of the emission end 116 so that the spectral components of the interference light LC are properly projected on the CCD elements and further automatically tailor the received-light amount to the target value. In addition, this operational example is effective if the specified received-light amount is relatively large (e.g., if the attenuator 121 does not defilade the reference optical path at the initial stage).

In the operational example above, although the emission end 116 is led to the intermediate position between the two positions indicated by the first and second positional information (S38, S39), the present invention is not limited to this processing. For example, taking into account the gradient (rate of change in the received-light amount relative to the movement of the emission end 116) in Step 32 (operation F1) and the gradient in Step 36: Yes (operation F3), the peak position of the received-light amount is estimated and the emission end 116 may be moved to this estimated position.

In the operational example above, although the attenuator 121 is adjusted while monitoring the received-light amount (S40), the present invention is not limited to this processing. An example thereof is described below.

First, the main controller 211 calculates the interval (i.e., a distance) L between these two positions based on the first and second positional information.

Next, the main controller 211, based on the interval L, calculates the amount of change in the light amount of the reference light LR (i.e., interference light LC) required to change the received-light amount from the limit value to the target value. This amount of change is the value which is, in the position of the emission end 116 when the received-light amount reaches a peak (i.e., proper position), required to decrease the received-light amount from the peak value to the target value. This amount of change can be obtained by, for example, estimating the peak value for the received-light amount based on the two positions above and the inclination above etc., and calculating the difference between the peak value and the target value.

Subsequently, the main controller 211 moves the emission end 116 to the proper position (the position corresponding to the peak), and further controls the attenuator 121 to decrease the light amount by the amount of change.

According to such processing, the amount of change in the light amount can be calculated to change at once, so it is not necessary to adjust the attenuator 121 while monitoring the received-light amount as in the operational example above, making it possible to attempt to reduce the processing time.

Actions and Effects

The actions and effects of the fundus observation apparatus 1 as described above will be described.

The fundus observation apparatus 1 is an optical image measurement apparatus of the Fourier domain type that detects the spectral components of the interference light LC and forms an OCT image of the fundus Ef. The fundus observation apparatus 1 comprises the received-light-amount specifying part 212 that specifies the received-light amount of the spectral components by the CCD image sensor 120.

The fundus observation apparatus 1 comprises the fiber-end drive mechanism 140 that changes the relative position between the emission end 116 of the optical fiber 115 that guides the interference light LC and the light-receiving surface of the CCD image sensor 120. In this embodiment, although moving the emission end 116 changes the relative position, the configuration is adequate if it is capable of moving at least one of the emission end 116 and the CCD image sensor 120. Moreover, the configuration may be able to change the optical relative position between the emission end 116 and the light-receiving surface by moving an optical member (such as the diffraction grating 118) disposed between the emission end 116 and the CCD image sensor 120.

Furthermore, the fundus observation apparatus 1 comprises the attenuator 121 that changes the light amount of interference light LC projected onto the CCD image sensor 120 by changing the light amount of reference light LR. In addition, it is possible to configure at least one of the light amount of low-coherence light L0, the light amount of signal light LS, the light amount of reference light LR, and the light amount of interference light LC to be changeable so as to achieve a similar action. In either case, the attenuator (second changing part) is adequate if it operates to change the light amount of interference light LC projected onto the CCD image sensor 120, and its specific configuration and location of placement do not matter.

The fundus observation apparatus 1 controls the fiber-end drive mechanism 140 and the attenuator 121 based on the received-light amount that is specified by the received-light-amount specifying part 212, and leads the received-light-amount of interference light LC by the CCD image sensor 120 to a target value P. Afterwards, the fundus observation apparatus 1 performs OCT measurement and forms an OCT image of the fundus Ef.

According to such a fundus observation apparatus 1, by adjusting the projection position of the interference light LC relative to the light-receiving surface and adjusting the light amount of interference light LC projected onto the CCD image sensor 120 (i.e., toward the CCD image sensor 120), the received-light amount can be automatically adjusted. Thus, it is possible to easily and quickly adjust the received-light amount.

In the first operational example of the fundus observation apparatus 1 (see FIG. 4 and FIG. 5), essentially the following four operations are executed. In addition, the first and second operations are executed by controlling the fiber-end drive mechanism 140 and the attenuator 121, respectively, with reference to the received-light amount sequentially specified by the received-light-amount specifying part 212. The first and second operations are executed alternately.

(The first operation) The relative position between the emission end 116 and the light-receiving surface (herein, the position of the emission end 116) is changed so as to increase the received-light amount to at least an upper limit in a predefined range. Particularly, in this embodiment, the operation to change the aforementioned relative position in a predefined direction by a predefined distance (unit moving distance) and the operation to change the received-light amount of interference light LC are performed alternately until the received-light amount above the upper limit is specified by the received-light-amount specifying part 212.

(The second operation) The amount of interference light LC (herein, reference light LR) is changed so as to decrease the received-light amount to at least a lower limit in the predefined range. Particularly, in this embodiment, the operation to decrease the light amount of reference light LR by a predefined amount (unit decrease amount) and the operation to specify the received-light amount of interference light LC are performed alternately until the received-light amount below the lower limit is specified by the received-light-amount specifying part 212.

(The third operation) When the received-light amount specified by the received-light-amount specifying part 212 decreases in response to the change in the relative position in the first operation, the fiber-end drive mechanism 140 is controlled to return the relative position to the status just prior to the change. Particularly, in this embodiment, moving the emission end 116 in a direction opposite to the predefined direction in the first operation changes the aforementioned relative position to the immediately preceding status.

(The fourth operation) By controlling the attenuator 121 to change the light amount of interference light LC, the received-light amount is led to a target value. Particularly, in this embodiment, controlling the attenuator 121 while sequentially specifying the received-light amount with the received-light-amount specifying part 212 leads the received-light amount to the target value.

According to such a first operational example, while automatically adjusting the light amount of interference light LC, the position to receive the spectral components can be automatically adjusted and, furthermore, the received-light amount can be automatically tailored to the target value, making it possible to easily and quickly adjust the received-light amount.

In the second operational example of the fundus observation apparatus 1 (see FIG. 6 and FIG. 7), first, by controlling the fiber-end drive mechanism 140 to change the relative position in a predefined direction with reference to the received-light amount that is sequentially specified by the received-light-amount specifying part 212, the peak of the specified received-light amount is detected. This peak is the maximum value for the received-light amount and corresponds to the aforementioned proper position. The peak of the received-light amount is detected by looking for the position where the received-light amount, which has increased with the movement of the emission end 116, shifts to decrease. The position that has been looked for is stored in the storage 213.

Next, the main controller 211 controls the fiber-end drive mechanism 140 in response to the peak being detected, moves the emission end 116 in the direction opposite to the predefined direction above, and disposes it in the position where the peak has been detected. This processing can be realized by, for example, reading the aforementioned position that has been looked for and moving the emission end 116 to this position.

Then, the main controller 211 controls the attenuator 121 to change the light amount of interference light LC and leads the received-light amount to the target value. This processing is executed, for example, in a similar manner to the fourth operation above.

According to such a second operational example, the position to receive the spectral components can be automatically adjusted and furthermore the received-light amount can be automatically tailored to the target value, making it possible to easily and quickly adjust the received-light amount. In addition, as described previously, the second operational example is effectively used, particularly if the specified received-light amount is relatively low.

In the third operational example of the fundus observation apparatus 1 (see FIG. 8 and FIG. 9), first, by controlling the fiber-end drive mechanism 140 while sequentially specifying the received-light amount, the relative position between the emission end 116 and the light-receiving surface is changed in a predefined direction. Thereby, the received-light amount is increased until it reaches the limit value for the CCD image sensor 120.

Next, the main controller 211 further changes the aforementioned relative position in a predefined direction until the specified received-light amount becomes less than the limit value.

Subsequently, the main controller 211 controls the fiber-end drive mechanism 140 and changes the relative position between the emission end 116 and the light-receiving surface to the relative position (third relative position) between the relative position (first relative position) when the received-light amount reaches the limit value and the relative position (second relative position) when it becomes less than the limit value. In this embodiment, the position of the emission end 116 when the received-light amount reaches the limit value is applied as the first relative position, the position of the emission end 116 when the received-light amount becomes less than the limit value as the second relative position, and the intermediate position between these two positions as the third relative position, respectively.

Finally, the main controller 211 controls the attenuator 121 to change the light amount of interference light LC and leads the received-light amount to the target value. This processing is executed in a similar manner to the fourth operation above, for example. Moreover, based on the interval between the first relative position and the second relative position, the amount of change in the light amount of interference light LC for changing the specified received-light amount from the limit value (actually peak value) to the target value may be calculated, and the light amount may be changed by this amount of change.

According to such a third operational example, the position to receive the spectral components can be automatically adjusted and, furthermore, the received-light amount can be automatically tailored to the target value, so it is possible to easily and quickly adjust the received-light amount. In addition, as described previously, the third operational example is effectively used particularly if the specified received-light amount is relatively high.

Modified Example

The configuration described above is merely one example for favorably implementing the present invention. It is possible for a person who intends to implement the present invention to properly make arbitrary modification within the scope of the present invention.

In the above embodiment, the position of the reference mirror 114 is changed so as to change an optical path length difference between the optical path of the signal light LS and the optical path of the reference light LR. However, a method for changing the optical path length difference is not limited thereto. For example, it is possible to change the optical path length difference by moving the retinal camera unit 2 and the OCT unit 100 with respect to the eye E to change the optical path length of the signal light LS. Moreover, in a case that an object is not a living site or the like, it is also effective to change the optical path length difference by moving the object in the depth direction (z-direction).

The control program 214 used in the above embodiments can be stored in any kind of recording medium that can be read by a computer. As this recording medium, for example, an optical disk, a magneto-optic disk (CD-ROM, DVD-RAM, DVD-ROM, MO, and so on), and a magnetic storage (a hard disk, a Floppy Disk™, ZIP, and so on) can be used. Moreover, it is possible to store into a storing device such as a hard disk drive and a memory.

In addition, it is possible to transmit/receive the control program 214 through a network such as internet or LAN etc.

EXPLANATION OF SYMBOLS

1 fundus observation apparatus
2 retinal camera unit
3 display device
10 illumination optical system
11 observation light source
15 imaging light source
30 imaging optical system
31 focusing lens
35, 38 CCD image sensor
39 LCD
43, 44 Galvano mirror
50 alignment optical system
60 focus optical system
70 scan driver
80 focus driver
100 OCT unit
101 light source unit
114 reference mirror
118 diffraction grating
120 CCD image sensor
121 attenuator
130 reference driver
140 fiber-end drive mechanism
200 arithmetic and control unit
210 controller
211 main controller
212 received-light-amount specifying part
213 storage
214 control program
220 image forming part
230 image processor
240 display
250 operation part
E eye
Ef fundus
K observation image
H photographed image
G tomographic image

What is claimed is:
1. An optical image measurement apparatus comprising:
an interferometer that splits light from a light source into signal light and reference light and generates interference light by superposing the signal light that has passed through a measured object and the reference light that has passed through a reference optical path;
a light guiding part that guides the generated interference light;
a spectral part that divides the interference light emitted from an emission end of the light guiding part into spectra;
a light-receiving part that receives the interference light divided into spectra and outputs a signal;
a specifying part that specifies a received-light amount of the interference light by the light-receiving part based on the output signal;
a first changing part that changes the relative position between the emission end and a light-receiving surface of the light-receiving part;
a second changing part for changing the light amount of the interference light projected onto the light-receiving part;
a controller configured to control the first changing part and the second changing part based on the specified received-light amount and lead the received-light amount of the interference light by the light-receiving part to a target value; and
an image forming part that forms an image of the measured object based on the results of the interference light received by the light-receiving part after the received-light amount has been led to the target value,
wherein the first changing part and the second changing part alternately perform the following operations:
a first operation where the first changing part changes the relative position to increase the received-light amount to at least an upper limit in a predefined range with reference to the received-light amount that is sequentially specified by the specifying part; and
a second operation where the second changing part changes the light amount to decrease the received-light amount to at least a lower limit in the predefined range,
wherein when the specified received-light amount decreases in response to a change in the relative position in the first operation, the first changing part performs a third operation that changes the relative position to the immediately preceding status of this change; and the second changing part then performs a fourth operation that changes the light amount and leads the received-light amount to the target value.

2. The optical image measurement apparatus according to claim 1, wherein the controller controls the first changing part based on the received-light amount specified by the specifying part and changes the relative position to increase the received-light amount.

3. The optical image measurement apparatus according to claim 1, wherein:
the light-receiving part is a line sensor that has multiple light-receiving elements arranged one-dimensionally; and
the first changing part changes the relative position by moving the emission end and/or the light-receiving part in a direction intersecting the direction of the arrangement of the multiple light-receiving elements.

4. The optical image measurement apparatus according to claim 1, wherein the second changing part comprises:
a shielding member that shields part of the cross-section of the light from the light source, the signal light, the reference light and/or the interference light; and
a drive part that moves the shielding member; and
wherein, the controller controls the drive part based on the received-light amount specified by the specifying part and moves the shielding member to change a shield region in the cross-section.

5. The optical image measurement apparatus according to claim 1, wherein the controller in the first operation causes the following operations to be performed alternately until the received-light amount above the upper limit is specified by the specifying part:
an operation that causes the first changing part to change the relative position in a predefined direction by a predefined distance; and
an operation that causes the specifying part to specify the received-light amount.

6. The optical image measurement apparatus according to claim 1, wherein the controller in the second operation causes the following operations to be performed alternately until the received-light amount below the lower limit is specified by the specifying part:
an operation that causes the second changing part to decrease the light amount by a predefined amount; and
an operation that causes the specifying part to specify the received-light amount.

7. The optical image measurement apparatus according to claim 1, wherein the controller in the third operation causes the first changing part to change the relative position to the immediately preceding status in a direction opposite to the predefined direction.

8. An optical image measurement apparatus comprising:
an interferometer that splits light from a light source into signal light and reference light and generates interference light by superposing the signal light that has passed through a measured object and the reference light that has passed through a reference optical path;
a light guiding part that guides the generated interference light;
a spectral part that divides the interference light emitted from an emission end of the light guiding part into spectra;
a light-receiving part that receives the interference light divided into spectra and outputs a signal;
a specifying part that specifies a received-light amount of the interference light by the light-receiving part based on the output signal;
a first changing part that changes the relative position between the emission end and a light-receiving surface of the light-receiving part;
a second changing part for changing the light amount of the interference light projected onto the light-receiving part;
a controller configured to control the first changing part and the second changing part based on the specified received-light amount and lead the received-light amount of the interference light by the light-receiving part to a target value; and
an image forming part that forms an image of the measured object based on the results of the interference light received by the light-receiving part after the received-light amount has been led to the target value,
wherein the controller, with reference to the received-light amount that is sequentially specified by the specifying part, by controlling the first changing part and changing the relative position in a predefined direction, detects the peak of the specified received-light amount;
the first changing part changes the relative position to the position where the peak has been detected in a direction opposite to the predefined direction in response to the peak being detected; and
the second changing part changes the light amount to lead the received-light amount to the target value.

9. An optical image measurement apparatus comprising:
an interferometer that splits light from a light source into signal light and reference light and generates interference light by superposing the signal light that has passed through a measured object and the reference light that has passed through a reference optical path;
a light guiding part that guides the generated interference light;
a spectral part that divides the interference light emitted from an emission end of the light guiding part into spectra;
a light-receiving part that receives the interference light divided into spectra and outputs a signal;
a specifying part that specifies a received-light amount of the interference light by the light-receiving part based on the output signal;
a first changing part that changes the relative position between the emission end and a light-receiving surface of the light-receiving part;
a second changing part for changing the light amount of the interference light projected onto the light-receiving part;
a controller configured to control the first changing part and the second changing part based on the specified received-light amount and lead the received-light amount of the interference light by the light-receiving part to a target value; and
an image forming part that forms an image of the measured object based on the results of the interference light received by the light-receiving part after the received-light amount has been led to the target value,
wherein the controller, with reference to the received-light amount that is sequentially specified by the specifying part, by controlling the first changing part and changing the relative position in a predefined direction, increases the received-light amount until reaching a limit value for the light-receiving part;
the first changing part further changes the relative position in the predefined direction until the specified received-light amount becomes less than the limit value;
the first changing part changes the relative position between the emission end and the light-receiving surface of the light-receiving part to a third relative position between a first relative position where the received-light amount reaches the limit value and a second relative position where it becomes less than the limit value; and the first changing part changes the light amount to lead the received-light amount to the target value.

10. The optical image measurement apparatus according to claim 9, wherein the third relative position is an intermediate position between the first relative position and the second relative position.

11. The optical image measurement apparatus according to claim 9, wherein the controller, in the operation leading the received-light amount to the target value, controls the second changing part with reference to the received-light amount that is sequentially specified by the specifying part.

12. The optical image measurement apparatus according to claim 9, wherein the controller:
- based on an interval between the first relative position and the second relative position, calculates the amount of change in the light amount for changing the specified received-light amount from the limit value to the target value; and
- in the operation leading the received-light amount to the target value, controls the second changing part to change the light amount by the calculated amount of change.

* * * * *